United States Patent
Maurya et al.

(10) Patent No.: US 8,669,232 B2
(45) Date of Patent: Mar. 11, 2014

(54) **FLAVONOL COMPOUNDS, A BIOACTIVE EXTRACT/FRACTION FROM *ULMUS WALLICHIANA* AND ITS COMPOUNDS FOR PREVENTION FOR TREATMENT OF OSTEO-HEALTH RELATED DISORDERS**

(75) Inventors: Rakesh Maurya, Lucknow (IN); Preeti Rawat, Lucknow (IN); Kunal Sharan, Lucknow (IN); Jawed Akhtar Siddiqui, Lucknow (IN); Gaurav Swarnkar, Lucknow (IN); Geetanjali Mishra, Lucknow (IN); Lakshmi Manickavasagam, Lucknow (IN); Girish Kumar Jain, Lucknow (IN); Kamal Ram Arya, Lucknow (IN); Naibedya Chattopadhyay, Lucknow (IN)

(73) Assignee: Council of Scientific & Industrial Research, New Delhi (IN)

( * ) Notice: Subject to any disclaimer, the term of this patent is extended or adjusted under 35 U.S.C. 154(b) by 363 days.

(21) Appl. No.: 12/920,927

(22) PCT Filed: Mar. 3, 2009

(86) PCT No.: PCT/IN2009/000146
§ 371 (c)(1),
(2), (4) Date: Jan. 20, 2011

(87) PCT Pub. No.: WO2009/110003
PCT Pub. Date: Sep. 11, 2009

(65) Prior Publication Data
US 2011/0112042 A1 May 12, 2011

(30) Foreign Application Priority Data
Mar. 5, 2008 (IN) .............................. 534/DEL/2008

(51) Int. Cl.
*A61K 31/70* (2006.01)
*A61K 31/7028* (2006.01)
*A61K 31/7042* (2006.01)
*C07H 1/08* (2006.01)

(52) U.S. Cl.
USPC .......................................................... 514/23

(58) Field of Classification Search
USPC ...................... 514/23, 1.11; 536/8, 128, 1.11
See application file for complete search history.

(56) References Cited

U.S. PATENT DOCUMENTS

2003/0109462 A1 6/2003 Kashiwaba et al.
2008/0003300 A1 1/2008 Gaffar

FOREIGN PATENT DOCUMENTS

CN 101058594 A 10/2007
EP 1 514 540 A1 3/2005

OTHER PUBLICATIONS

Kwon et al. (Archives of Pharmacal Research (2004), 27(7), 751-756).*
KR Arya, et al; "Folk Therapy for Eczema, Bone Fracture, Boils, Sores, and Gingivitis in Taragtal Province of Uttaranchal", Indian Journal of Traditional Knowledge, vol. 7(3), Jul. 2008, pp. 443-445.
Pierre D Delmas; "Treatment of Postmenopausal Osteoporosis", The Lancet; vol. 359, Jun. 8, 2002; pp. 2018-2026; www.thelancet.com.
R.D. Gaur, "Flora of the District Garhwal North West Himalaya (With Ethnobotanical Notes)", TransMedia Srinagar (Garhwal)—246 174; U.P. India, 1999; 1 page.
Dr. S.K. Jain; "Section 1: Ethnobotanical Uses of Plants", Dictionary of Indian Folk Medicine and Ethnobotany A Reference Manual of Man-Plant Relationships, Ethnic Groups & Ethnobotanists in India (With 433 Illustrations), DEEP Publications, 1991, 1 page, p. 183.
Charlene Marais, et al; (S)- and (R)-Eriodictyol-6-C-β-D-glucopyranoside, novel keys to the fermentation of rooibos (*Aspalathus linearis*), Phytochemistry, Pergamon Press, GB, vol. 55, No. 1, Sep. 1, 2000, pp. 43-49, XP004291558; ISSN: 0031-9422 compounds 4A,4B.
B. Lawrence Riggs, M.D., et al; "Selective Estrogen-Receptor Modulators—Mechanisms of Action and Application to Clinical Practice", The New England Journal of Medicine, vol. 348; pp. 618-619, Feb. 13, 2003.

(Continued)

*Primary Examiner* — Shaojia Anna Jiang
*Assistant Examiner* — Michael C Henry
(74) *Attorney, Agent, or Firm* — Ladas & Parry LLP

(57) ABSTRACT

The present invention provides a flavonol compound and a bioactive extract/fraction from *Ulmus wallichiana* useful for the management or prevention or treatment of bone disorders. Said extract/fraction comprising marker compounds of general formula 2, K058: $R_1=R_2=OH$ K012: $R_1=R_2=OH$, 2,3 double bond K068: $R_1=R_2=H$ KIOOi $R_1=OH$, $R_2=H$ mula 2 Wherein the marker compounds K012, K058, K068, K1OO ranges 6.7-12%, 1.7-4.5%, 0.6-1.2%, 1.7-4.5% respectively in alcoholic extract and a process of extraction thereof. According to another aspect of the invention provides a pharmaceutical composition comprising the said compound. The present invention further provides a method of treating bone disorders by administering the pharmaceutical composition by oral, intravenous, subcutaneous, intra-peritoneal or intramuscular route.

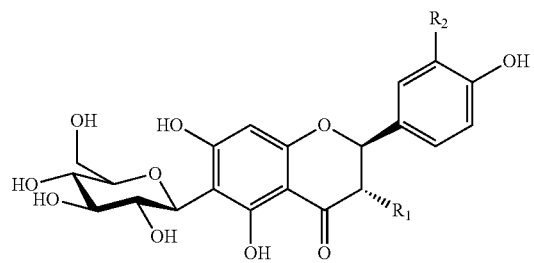

(II)

29 Claims, 19 Drawing Sheets

(56) References Cited

OTHER PUBLICATIONS

Figure 1:
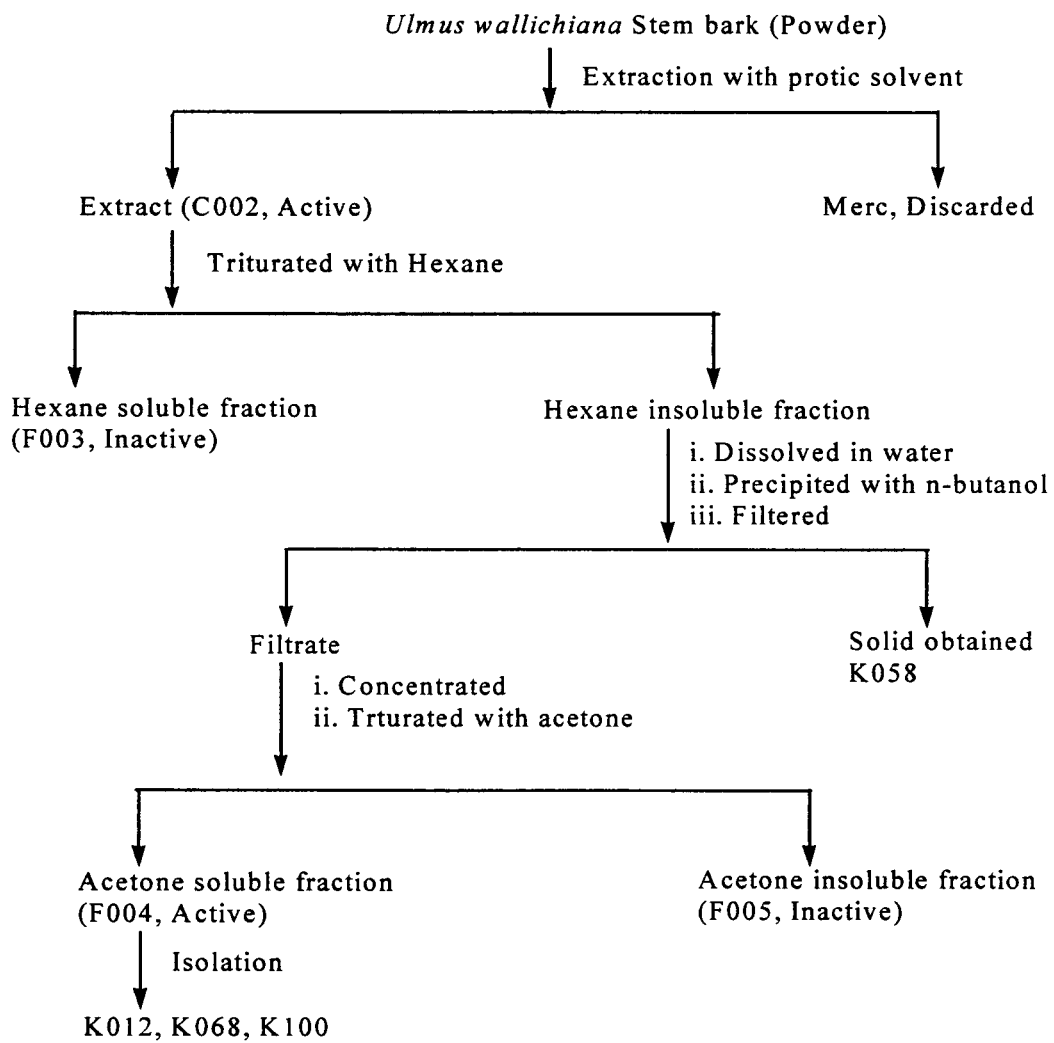
Figure 2A:
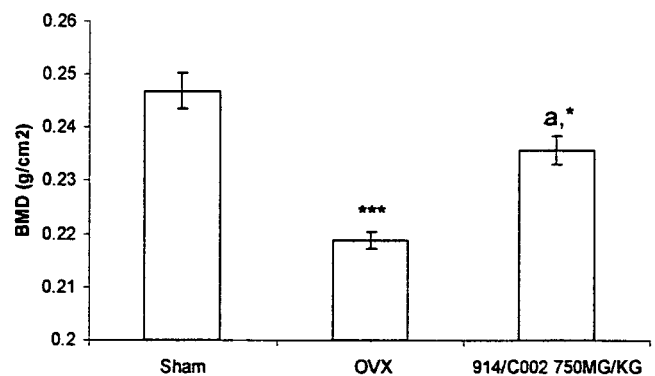
Figure 2B:
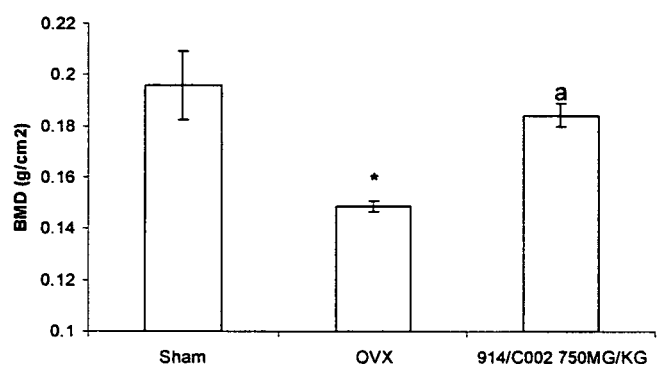
Figure 2C:
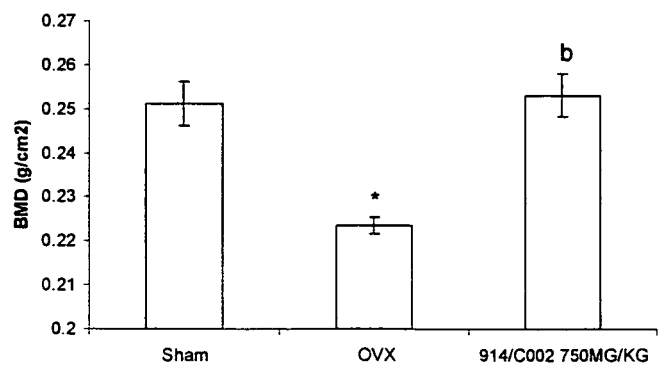
Figure 2D:
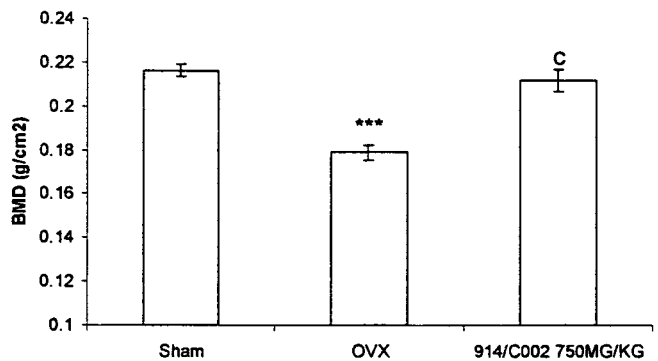

Leslie A. Soyka, et al; "Clinical Review 117 Hormonal Determinants and Disorders of Peak Bone Mass in Children", The Journal of Clinical Endocrinology and Metabolism, vol. 85, No. 11, Nov. 1, 2000, pp. 3951-3963.

Xin-Luan Wang, et al; "Effects of Eleven Flavonoids from the Osteoprotective Fraction of *Drynaria fortunei* (KUNZE) J. Sm. On Osteoblastic Proliferation Using an Osteoblast-Like Cell Line", Chemical & Pharmaceutical Bulletin, 56(1), 46-51 Coden: CPBTAL; ISSN: 0009-2363, 2008, XP009118209, the whole document.

J. Tanyi Mbafor, et al; "Isolation and Characterization of Taxifolin 6-C-Glucoside From Garcinia Epunctata", Journal of Natural Products, vol. 52, No. 2, pp. 417-419, Mar.-Apr. 1989.

S. Adami; "Optimizing Peak Bone Mass: What are the Therapeutic Possibilities?", Osteoporosis International, vol. 4, Suppl. 1: pp. S27-30; Jan. 1994.

Deborah Grady, et al; "Hormone Replacement Therapy and Endometrial Cancer Risk: A Meta-Analysis", Obstetrics & Gynecology, Feb. 1995, vol. 85, Issue 2, pp. 304-313.

Shirley A A Beresford, et al; "Risk of endometrial cancer in relation to use of oestrogen combined with cyclic progestagen therapy in postmenopausal women", The Lancet, vol. 349, Issue 9050, Feb. 15, 1997, pp. 458-461.

Delyth Clemett, et al; "Raloxifene A Review of its Use in Postmenopausal Osteoporosis" vol. 60(2), Aug. 2000, pp. 379-411.

International Search Report mailed Jun. 23, 2009; PCT/IN2009/000146.

M. Passeri, et al; "Effect of ipriflavone on bone mass in elderly osteoporotic women", Bone and Mineral, 19(Suppl.), pp. S57-S62, This paper was presented at a satellite symposium at the XIth International Conference on Calcium Regulating Hormones, held Apr. 24-29, 1992, Florence, Italy.

\* cited by examiner

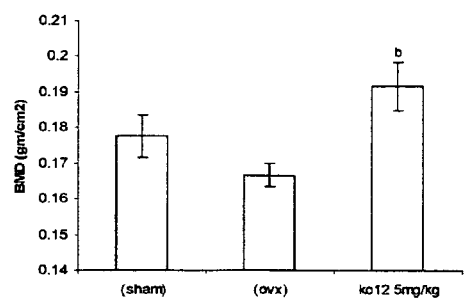
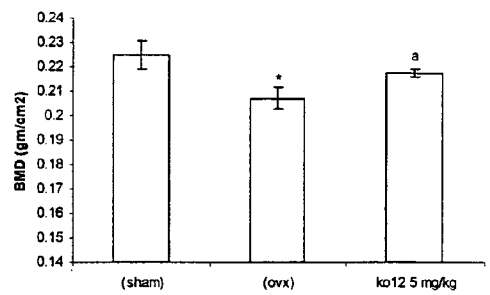
Fig 17 A
Fig 17 B
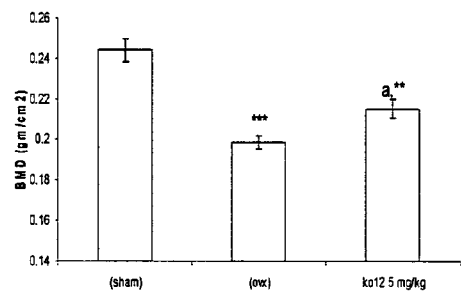
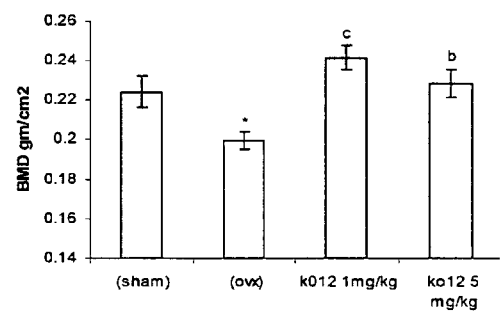
Fig 17 C
Fig 17 D
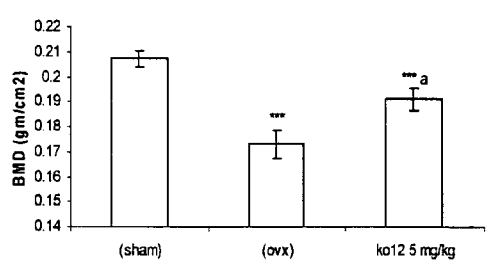
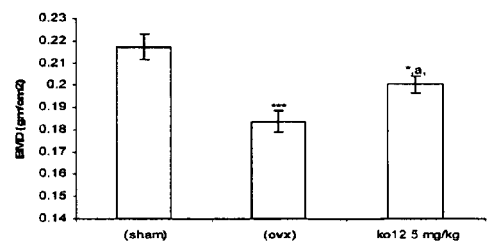
Fig 17 E
Fig 17 F

FLAVONOL COMPOUNDS, A BIOACTIVE EXTRACT/FRACTION FROM *ULMUS WALLICHIANA* AND ITS COMPOUNDS FOR PREVENTION FOR TREATMENT OF OSTEO-HEALTH RELATED DISORDERS

FIELD OF THE INVENTION

The present invention relates to the field of pharmaceutical composition that provides novel flavonol compounds, novel plant extracts, their fractions and pure compounds isolated from natural sources that are useful for the prevention and/or treatment of various medical indications associated with estrogen dependent or independent diseases or syndromes or disorders preferably in the prevention or treatment of estrogen dependent or independent diseases or syndromes or disorders caused in humans and animals, and achievement of peak bone mass (PBM) during skeletal growth and health in humans and animals. Particularly the present invention further relates to the processes for the preparation of biologically active extracts, fractions, and isolation of pure compounds, from *Ulmus wallichiana* plant from the family Ulmaceae, their pharmaceutically acceptable salts and compositions are of the principal aspect of the present invention.

BACKGROUND OF THE INVENTION

Osteoporosis, which has been defined as a "state of low bone mass" is one of the major aging problems of the society. Osteoporosis is a metabolic disorder characterized by microarchitectural deterioration of bone tissue leading to enhanced bone fragility and consequent increase in fracture risk in older members of the population. Osteoporosis fractures occur most commonly in the spine, hip, distal radius and ribs. The risk is high in women as compared to men and increases sharply after 50 years of age. Factors predisposing towards osteoporosis include family history, genetic factors, hormonal factors, inadequate nutrition, and intake of certain medications, immobility and disease. The quality of life is greatly impaired in persons with sever osteoporosis. It is known to affect >50% of women and 30% men over the age of 50 years. In women, there is also an accelerated rate of bone loss immediately and for variable number of years following menopause.

There is a well-recognized link between the prevalence of low PBM attainment and osteoporosis among South Asian women (S. Adami. *Osteoporosis Int.*, 1:S27-30, 1994). PBM is defined as the highest level of bone mass achieved as a result of normal growth. Adolescence is the most critical period across the life span for bone health because more than half of PBM is accumulated during the teenage years. During these early years of life, bone formation is greater than bone resorption and the bone mass increases. PBM attained in early adult life is an important determinant of skeletal fragility at least until the age of 70 years (L. A. Soyka, W. P. Fairfiled, A. Klibanski. *J Clin Endocrinol Metab*, 11:3951-3963, 2000). Following the attainment of PBM, resorption is faster than formation and the bone mass decreases. While gradual bone loss is normal to aging, it is those who fail to achieve optimal PBM and/or those with accelerated bone loss who are at the greatest risk of osteoporosis. In addition, low PBM predisposes to increased fragility fracture risk.

Therefore, since individuals with a high PBM at a young age are likely to have a high bone mass in old age, agents increasing PBM during skeletal growth is a desirable goal towards prevention of osteoporosis. PBM occurs several years after the completion of linear growth as bone mineral accretion continues after this time, although the precise timing of the attainment of PBM is not certain and varies between skeletal sites. Areal Bone mass density (BMD) at the femur peaks around the age of 20 yr, whereas maximum total skeletal mass occurs 6-10 yr later, well after the cessation of the anabolic action of growth hormone (GH).

Most of the pharmacological agents available for bone loss disorders include calcium, vitamin D and its analogues, calcitonin, bisphosphonates, raloxifene, hormone replacement therapy (HRT) etc. which act by decreasing the rate of bone resorption, thereby slowing the rate of bone loss. Timely administration of such antiresorptive agents prevents bone loss.

Hormone replacement therapy, though effective in preventing bone loss following ovariectomy or menopause in women, is associated with increased risk of endometrial hyperplasia and carcinoma [Grady, D. Grebretsadik, T. Ernestwr, V. Petitti, D. *Gynecol.* 85, 304-313 (1995), Beresford S. A. Weiss, N. S. Voigt, L. F. McKnight, B. *Lancet* 349, 458-461 (1997)], breast cancer [Riggs, L. Hartmann, L. C. *J. Med.* 348, 618-629, (2003)], and thromboembolic diseases [Delmas, P. D. *Lancet* 359, 2018-2026 (2002)].

The side effect of calcium therapy is development of renal stones. The major disadvantage in calcitonin use is its high cost. Tachyphylaxis can develop in some individuals under calcitonin treatment.

Bisphosphonates are poorly absorbed and may cause gastrointestinal irritation, diarrhoea and constipation. Raloxifene has been reported to increase incidence of hot flashes, deep vein thrombosis, pulmonary embolism and leg cramps [Clemett, D.; Spencer, C. M. *Drugs* 60, 380-409 (2000)].

Factors relating to the attainment of PBM include congenital, dietary, hormonal, physical activity, lifestyle, drugs and diseases. A therapeutic intervention aimed at increasing PBM has remained limited only to controlling factors such as estrogen status, dietary calcium intake and physical activity. Calcium intake appears to be relevant up to the so-called threshold intake (1000 mg/day), but higher allowances do not seem to offer additive advantages. Exercise affects only the regions of the skeleton under mechanical stress. Estrogen administration is realistic only in conditions characterized by severe hypoestrogenism. Clearly, nutritional deficiency is one of the major reasons for lack of PBM among South Asians, particularly among females those who are much more prone to bone loss at later stages of life. Therefore, agents that promote PBM have therapeutic implication for bone loss disorders.

In view of the use of these therapies and their associated side effects indicate a need for the alternative options in the prevention and treatment of osteoporosis and failure to achieve PBM.

Traditional medicine is an ancient medical practice that existed in human societies before the application of modern science to health. The importance of traditional medicine as a source of primary health care was first officially recognized by the World Health Organization (WHO) in 1976 by globally addressing its Traditional Medicine Programme. In traditional medicine, there are many natural crude drugs that have the potential to treat bone diseases. However, not much laboratory work has been reported evaluating their possible development and use, except ipriflavone, a natural product derivative, which has been used clinically for such indications [Fujita, T.; Yoshikawa, S.; Ono, K.; Inoue, T.; Orimo, H. *J. Clin. Exp. Med.* 138, 113-141 (1986), Passeri, M.; Biondi, M.; Costi, D.; Bufalino, L.; Castiglione, g. N.; DiPeppe, C.; Abate, G. *Bone Miner.* 19 (Suppl. 1), S57-62 (1992)]. It is believed that herbal medicines are easily available, less expensive, and safer than chemically synthesized drugs. In India Ayurvedic medicine emerged during the rise of the philosophies of the Upanishads, Buddhism, and other schools of thought in India. Herbs played an important role in Ayurvedic medicine. One such Ayurvedic herbal medicine is *Ulmus wallichiana* Planchon. In and around Kumaon traditional healers use this plant for promoting fracture healing [Gaur, R. D. Flora of District Garhwal, North West Himalaya. Trans Media, Srinagar (Garhwal), India, 1999, pp. 86; Arya, K. R.; Agarwal, S. C. Indian J. Traditional Knowledge, In Press], but the effects on osteoporosis and total osteo-health and related disorders and has not been scientifically explored.

There is, thus, an urgent need to discover and develop a promising herbal product or a single biologically active molecule based drug or a cocktail of the pure and biologically active molecules of the plant origin that exhibit promising bone anabolic or for bone forming activity in experimental animals and human beings. The *Ulmus wallichiana* was a fit case to study and explore its true potential with respect to its bone forming response of its extract, fraction and pure biologically active marker components. The experiments have shown that its crude extract, acetone soluble fraction and pure compounds isolated from the extract and the fraction exhibit promising bone forming activity.

The *Ulmus wallichiana* Planchon, belongs to family Ulmaceae, distributed through Himalayas from Afghanistan to W. Nepal [Dictionary of Indian Folk Medicine and Ethnobotany edited by Jain, S. K., Deep Publications, Paschim Vihar, New Delhi, India, 1991, pp 183]. Leaves of the plant yield fodder and bark yield strong fiber. In India this plant is found in Kumaon and Garhwal Himalaya, locally called as Chamarmou, is deciduous tree growing to 35 m in high. So far this plant has not been chemically and pharmacologically investigated.

OBJECTIVE OF THE INVENTION

The main object of the present invention is to prepare novel compounds, a bioactive extract/fraction from *Ulmus wallichiana* useful for the management or prevention or treatment of bone disorders.

Another object of the present invention is to identify the marker compounds of the bioactive extract/fraction.

Yet another object of the present invention is to provide the process for isolation of the individual components.

Still another object of the present invention is to provide the pharmaceutical composition for the prevention or treatment of estrogen dependent or independent diseases or syndromes or disorders caused in humans and animals, and achievement of peak bone mass (PBM) during skeletal growth and health in humans and animals.

SUMMARY OF THE INVENTION

The present invention relates to the field of pharmaceutical composition that provides novel flavonol compounds, novel plant extracts, their fractions and pure compounds isolated from natural sources that are useful for the prevention and/or treatment of various medical indications associated with estrogen dependent or independent diseases or syndromes or disorders preferably in the prevention or treatment of estrogen dependent or independent diseases or syndromes or disorders caused in humans and animals, and achievement of peak bone mass (PBM) during skeletal growth and health in humans and animals. Particularly the present invention further relates to the processes for the preparation of biologically active extracts, fractions, and isolation of pure compounds, from *Ulmus wallichiana* plant from the family Ulmaceae, their pharmaceutically acceptable salts and compositions of the principal aspect of the present invention.

BRIEF DESCRIPTION OF THE DIAGRAMS ASSOCIATED WITH THE INVENTION

FIG. 1: Flow diagram showing extraction, fractionation and isolation of crude extract and pure fractions from *Ulmus wallichiana* stem bark.

FIG. 2: Ethanolic extract of *Ulmus wallichiana* reduces Ovx-induced bone loss in rats. BMD (Bone Mass Density) was measured by DEXA in excised bones. Ovx rats treated with 750 mg/kg b.w. C002 for 90 days were compared with Ovx and sham operated rats treated with vehicle (control). (A) Femur global, (B) femur neck, (C) femur shaft and (D) fourth lumber vertebra (*—$P<0.001$, —$P<0.01$, *—$P<0.05$ when compared with the BMD of sham. a—$P<0.001$, b—$P<0.01$, c—$P<0.05$ when compared with the BMD of ovx control.).

Figure 3:
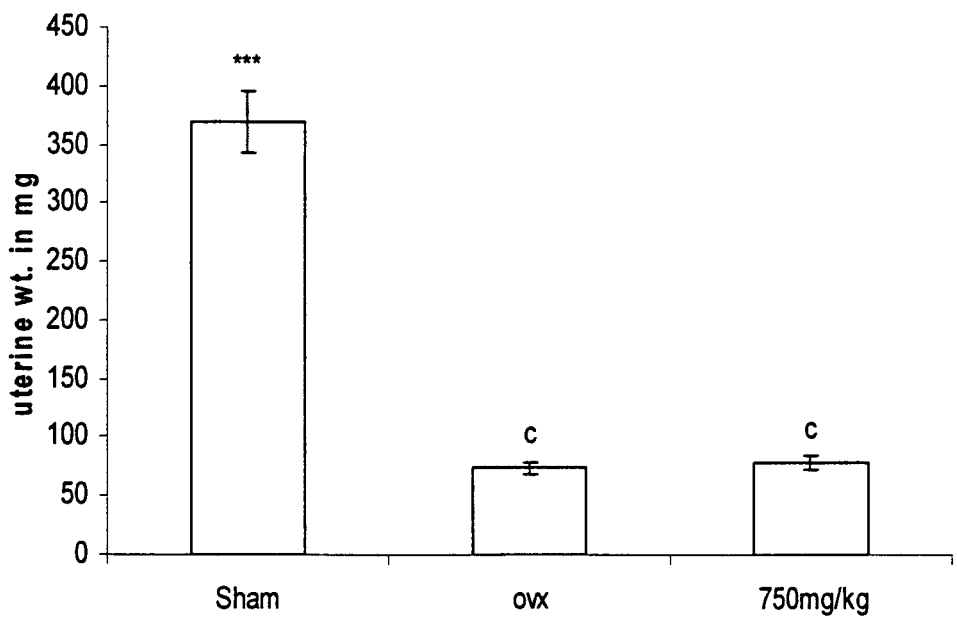

FIG. 3: Ethanolic extract of *Ulmus wallichiana* is not estrogenic in rats at uterine level. Uterine wt. of 750 mg/kg b.w. C002 treated rats for 90 days as compared to control sham and ovx rats. *—$P<0.001$, —$P<0.01$, *—$P<0.05$ when compared with uterine wt of sham control rats; c—$P<0.001$; b—$P<0.01$; a—$P<0.05$ when compared with uterine wt of ovx rats.

Figure 4:
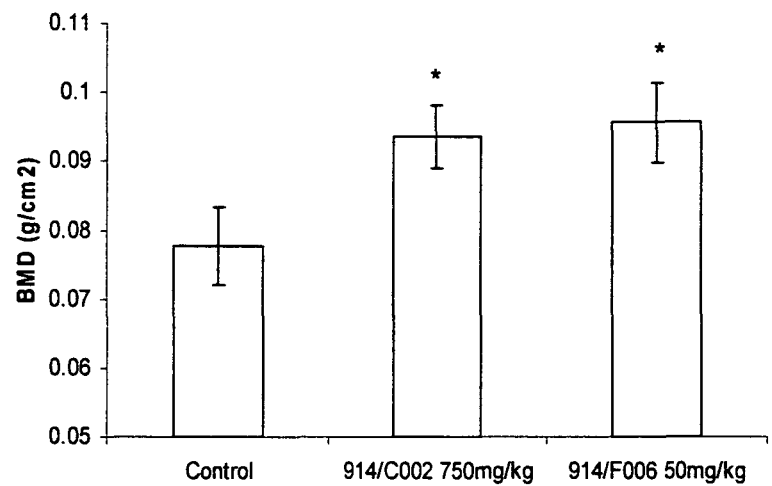
Figure 4:
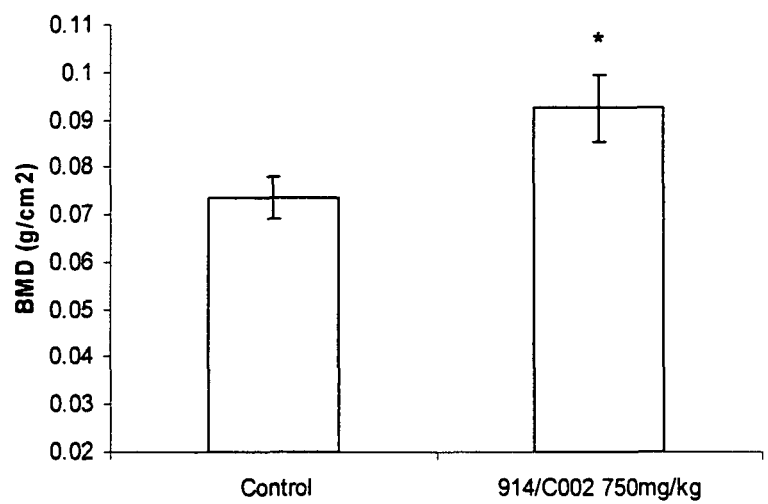

FIG. 4: Ethanolic extract and a fraction of *Ulmus wallichiana* promote PBM in immature rats. BMD was measured by DEXA in excised bones. (A) Femurs of growing female rats treated with 750 mg/kg C002 and 50 mg/kg 914/F006 (a fraction of 914/C002) were compared with vehicle (control) treated rats. (B) Fourth lumber vertebra of control and rats treated with 750 mg/kg 914/C002. (*—$P<0.001$, —$P<0.01$, *—$P<0.05$).

Figure 5:
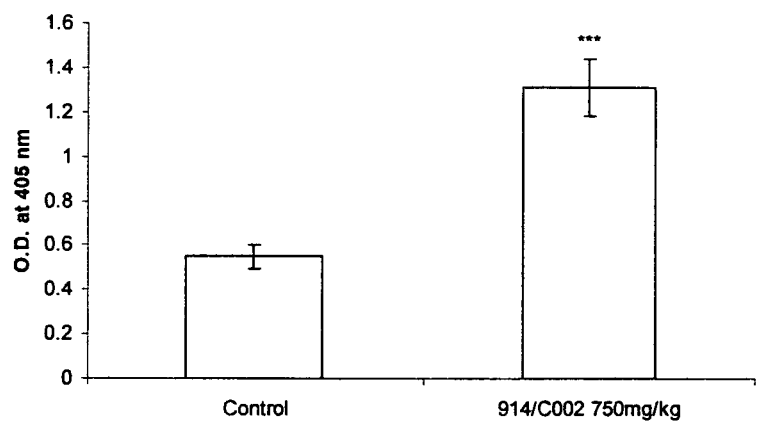
Figure 5:
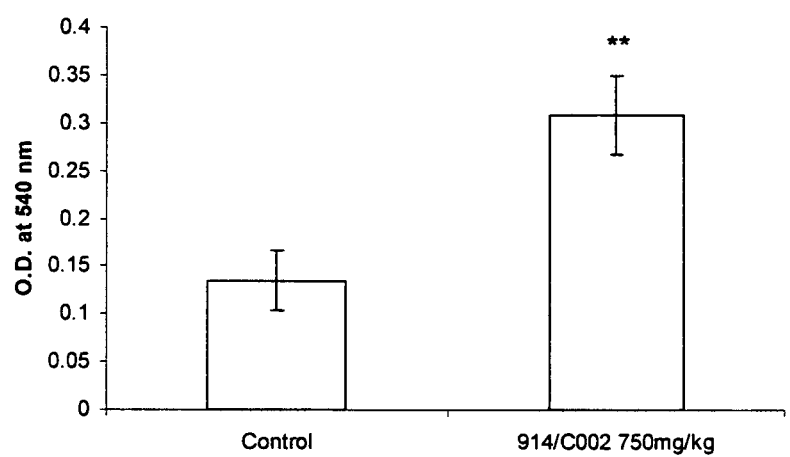
Figure 5:

FIG. 5: Ethanolic extract of *Ulmus wallichiana* promotes osteoprogenitor cells in immature rats. BMCs (Bone Marrow Cells) from growing female rats treated with 750 mg/kg 914/C002 were compared with vehicle (control) treated rats. (A) Alkaline phosphatase assay (for osteoblast differentiation), (B) photomicrographs of alizarin red-S stained cells (for osteoblast mineralization) and (C) quantification of alizarin red-S stain after extraction (*—$P<0.001$, —$P<0.01$, *—$P<0.05$).

Figure 6:
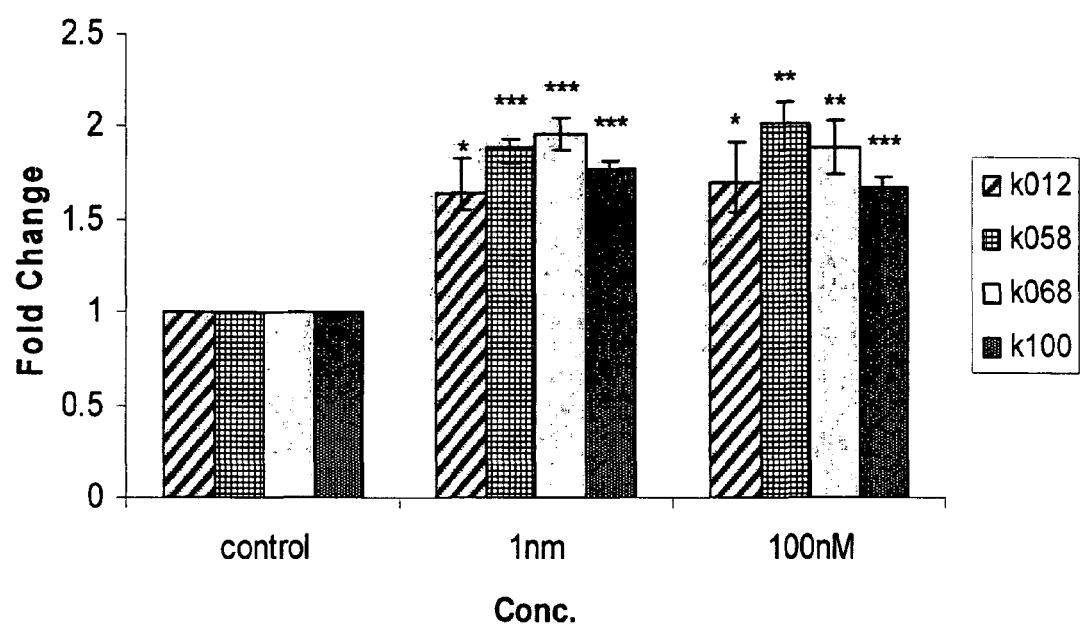

FIG. 6: Four pure compounds from *Ulmus wallichiana* promote differentiation of calvarial osteoblasts in vitro. Calvarial osteoblasts were treated with K012, K058, K068 and K100 at 1 and 100 nM concentrations and ALP (Alkaline Phosphatase) production was quantitated. *—$P<0.001$, —$P<0.01$, *—$P<0.05$; N=3.

Figure 7A:
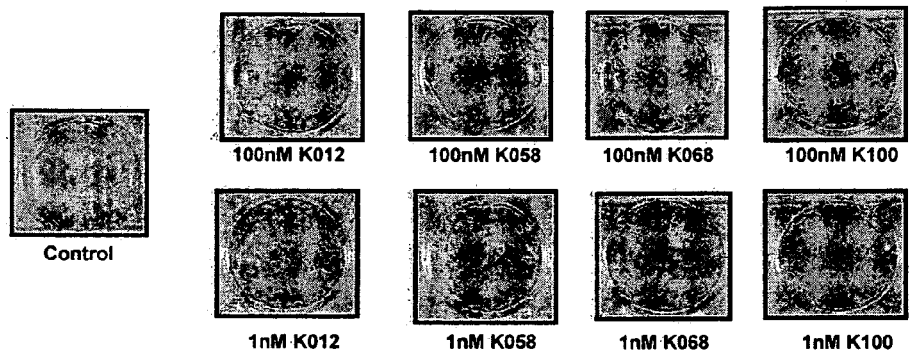
Figure 7B:
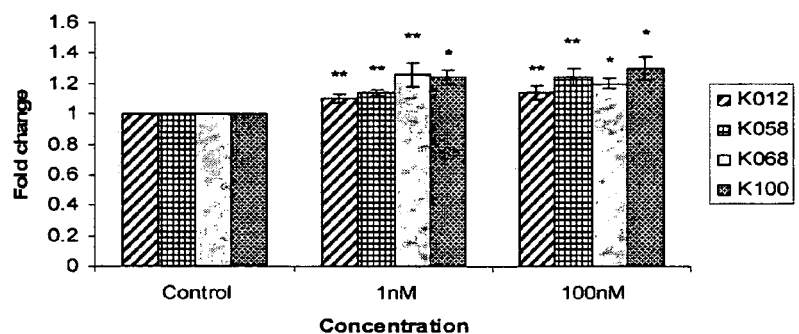

FIG. 7: Four pure compounds from *Ulmus wallichiana* promote in vitro mineralization of calvarial osteoblasts. Calvarial osteoblasts were treated with K012, K058, K068 and K100 at 1 and 100 nM concentrations. (A) Photomicrograph of osteoblasts stained with alizarin red-S. (B) Quantification of alizarin red-S stain after its, extraction (*—$P<0.001$, —$P<0.01$, *—$P<0.05$). (C) Photomicrograph of osteoblasts stained by von kossa method.

Figure 8:
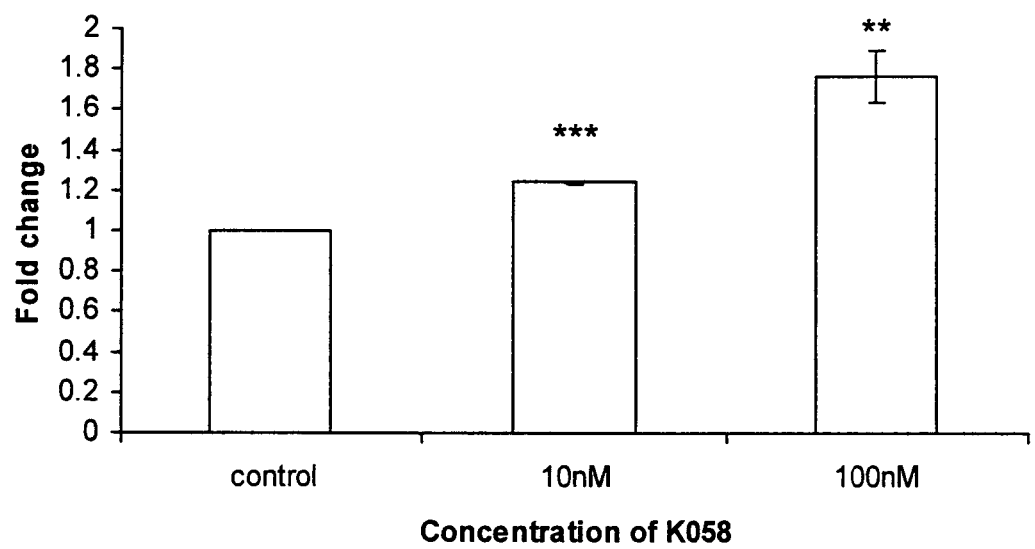

FIG. 8: K058 promotes proliferation of calvarial osteoblasts. Calvarial osteoblasts were treated with K058 at 1 and 100 nM concentration and BrdU cell proliferation assay was performed. *—$<0.001$, —$P<0.01$, *—$P<0.05$; N=3.

Figure 9:
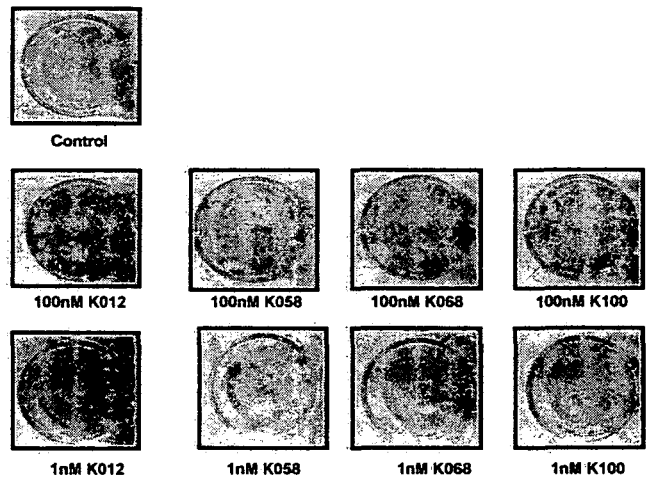
Figure 9:
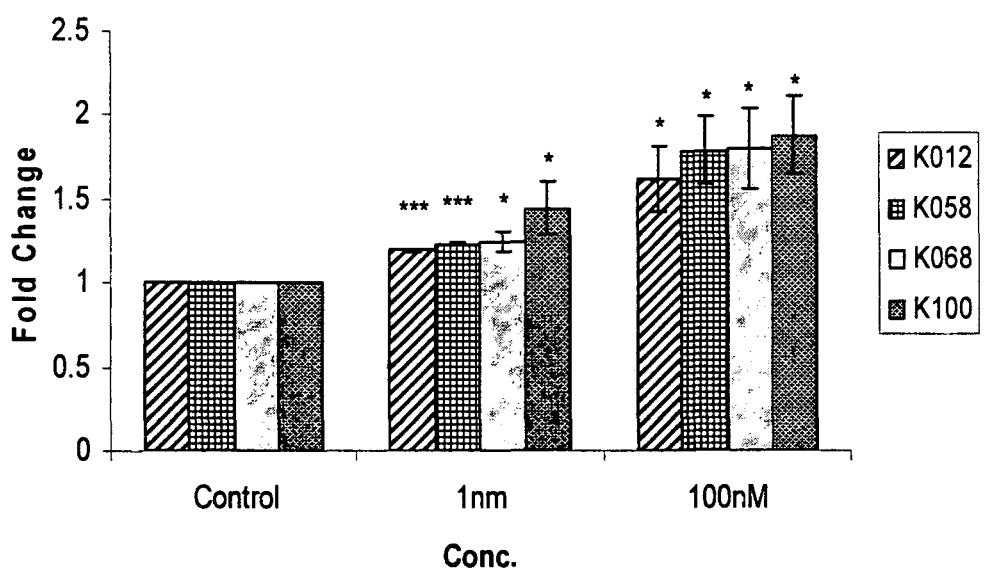

FIG. 9: Four pure compounds from *Ulmus wallichiana* promote in vitro mineralization of BMCs (Bone marrow cells). BMCs treated with K012, K058, K068 and K100 at 1 and 100 nM concentrations and mineralization was performed. (A) Photomicrograph of cells stained with alizarin red-S. (B) Quantification of alizarin red-S stain after its extraction (*—P<0.001, —P<0.01, *—P<0.05).

Figure 10:
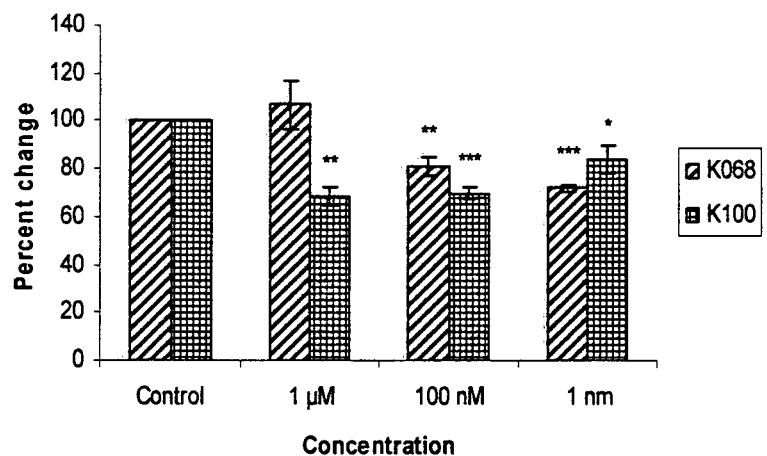
Figure 10:
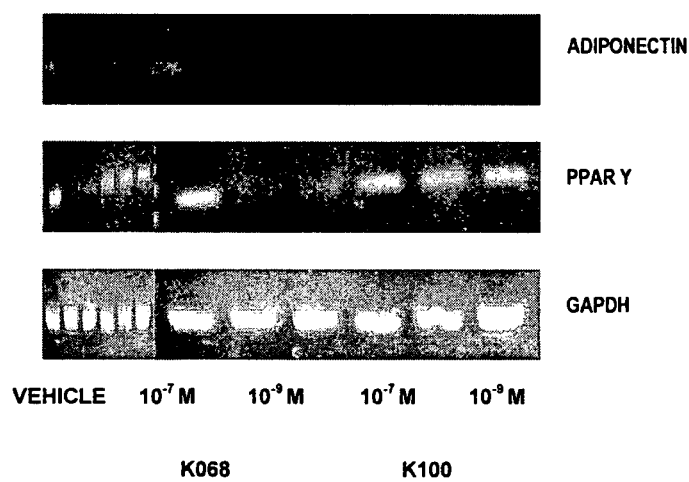

FIG. 10: K068 and K100 inhibit adipogenic differentiation of 3T3-L1 murine preadipocytes. (A) 3T3-L1 cells were treated with K068 and K100 at 1 μM, 100 nM and 1 nM concentrations and oil red-O staining was performed. Stain was extracted and quantitated. *—P<0.001, —P<0.01, *—P<0.05; N=3. (B) Semi-quantitative RT PCR of various adipocyte differentiation-specific genes following the treatment of 3T3-L1 preadipocyte cell with 100 nM and 1 nM of both K068 and K100 for 8 d (time of adipocyte differentiation). GAPDH was used as RNA loading control. Representative gel picture of three independent experiments with similar results.

Figure 11:
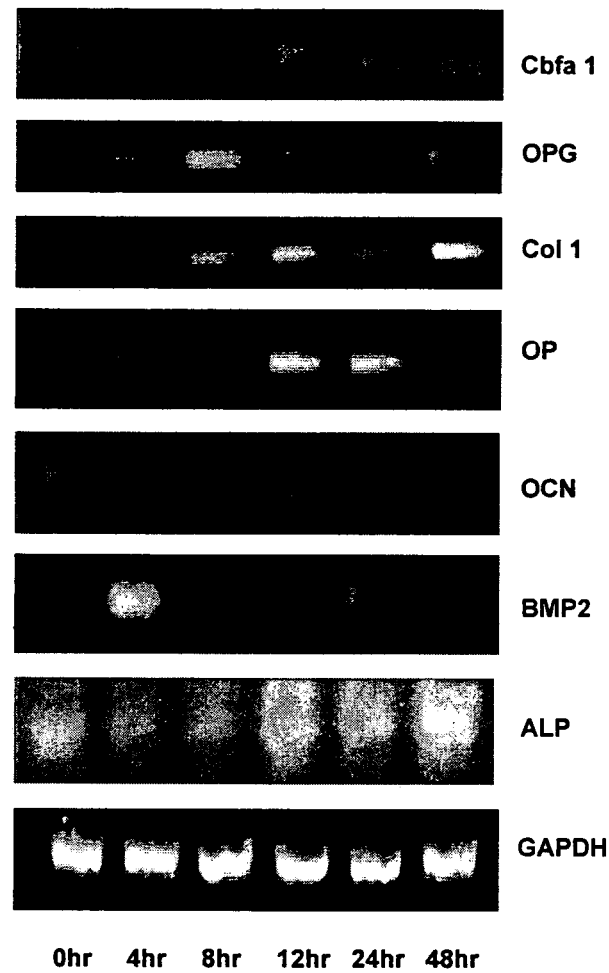

FIG. 11: K058 increases mRNA levels of various osteoblast-specific genes. Semi-quantitative RT PCR of various osteoblast mRNAs following the treatment of calvarial osteoblasts with 100 nM of K058 at various time points. GAPDH was used as internal loading control. Representative gel picture of three independent experiments with similar results.

Figure 12:
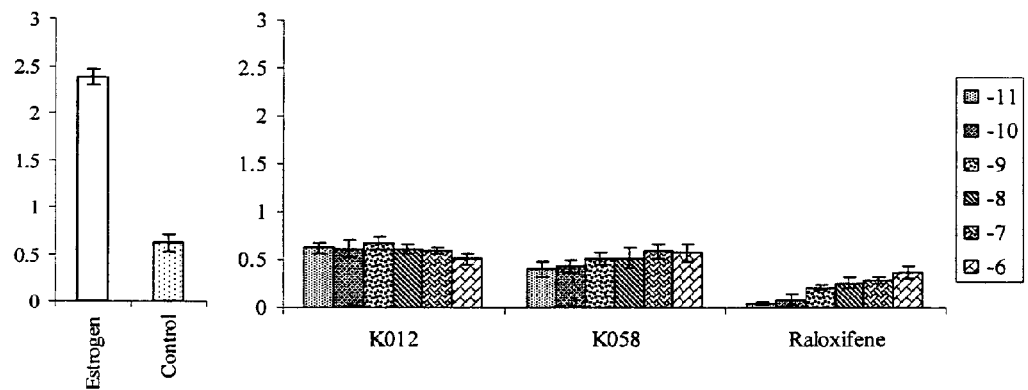
Figure 12:
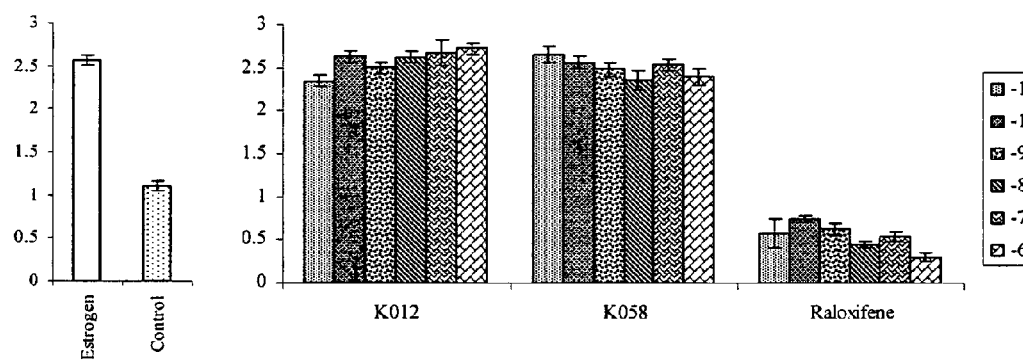

FIG. 12: K058 and K012 do not possess estrogenicity and anti-estrogenicity in vitro. Ishikawa cells treated with 17β-estradiol stimulates ALP production. (A) Robust increases in ALP (Alkaline phosphatase) with $10^{-8}$ M 17β-estradiol compared with control. K058, K012 and raloxifene at various concentrations have no response. (B) ALP levels with various concentrations of K012, K058 and raloxifene in the presence of $10^{-8}$ M 17β-estradiol.

Figure 13:
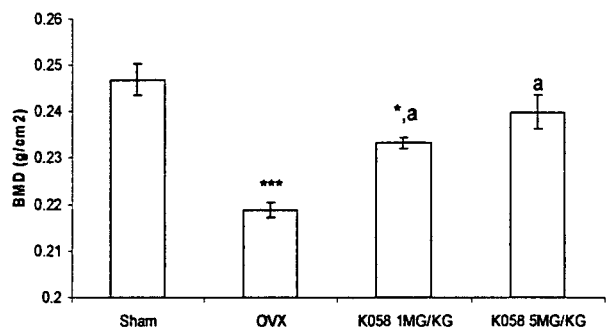
Figure 13:
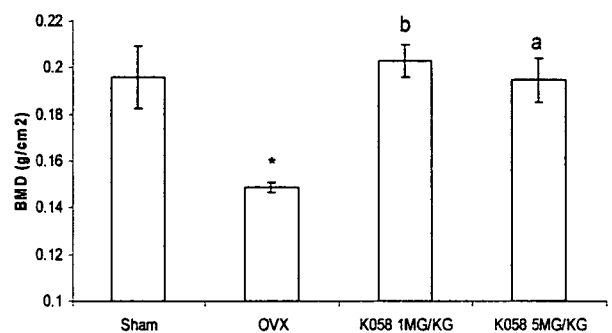
Figure 13:
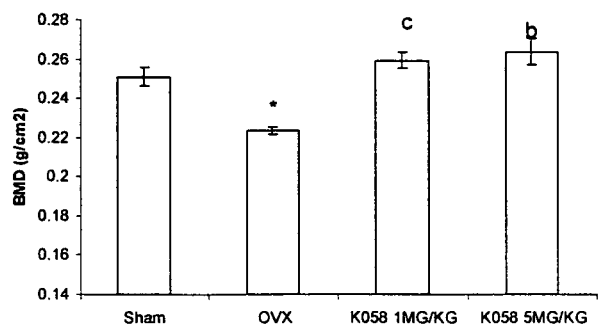
Figure 13:
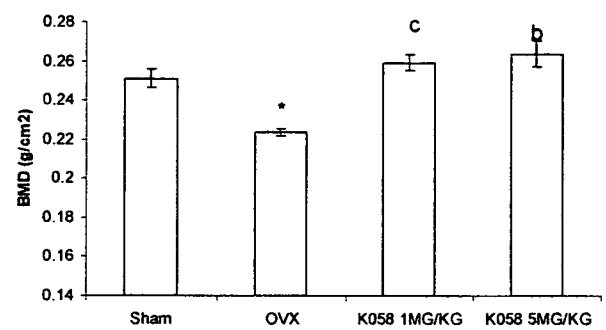
Figure 13:
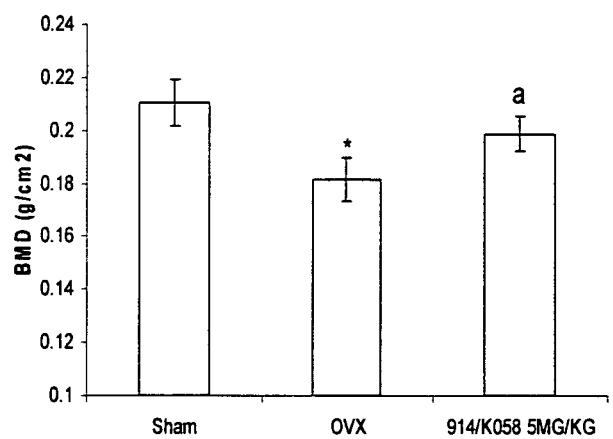

FIG. 13: K058 reduces Ovx-induced bone loss in rats. BMD was measured by DEXA in excised bones. Ovx rats treated with 1.0&5.0 mg/kg K058 for 90 days were compared with Ovx and sham operated rats treated with vehicle (control). (A) Femur global, (B) femur neck, (C) femur shaft, (D) fourth lumber vertebra and (E) tibia head (*—P<0.001, —P<0.01, *—P<0.05 when compared with the BMD of sham. a—P<0.001, b—P<0.01, c—P<0.05 when compared with the BMD of Ovx control).

Figure 14:
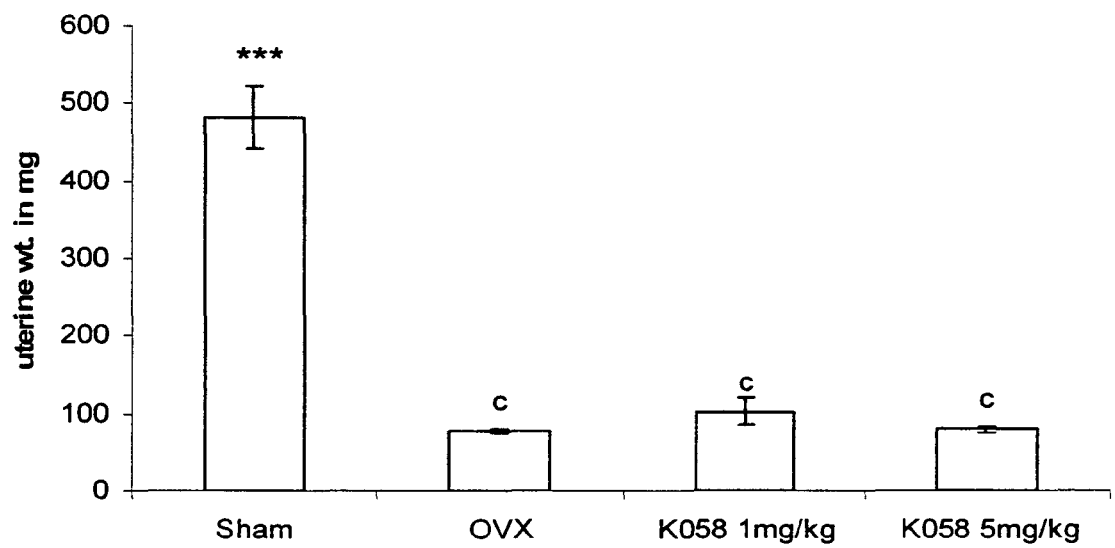

FIG. 14: K058 is not estrogenic in rats at uterine level. Uterine wt of 1.0&5.0 mg/kg body weight K058 treated rats for 90 days was compared with uterine weight of control sham and ovx rats. *—P<0.001, —P<0.01, *—P<0.05 when compared with uterine weight of sham control rats, c—P<0.001, b—P<0.01, a—P<0.05 when compared with uterine wt of ovx rats.

Figure 15:
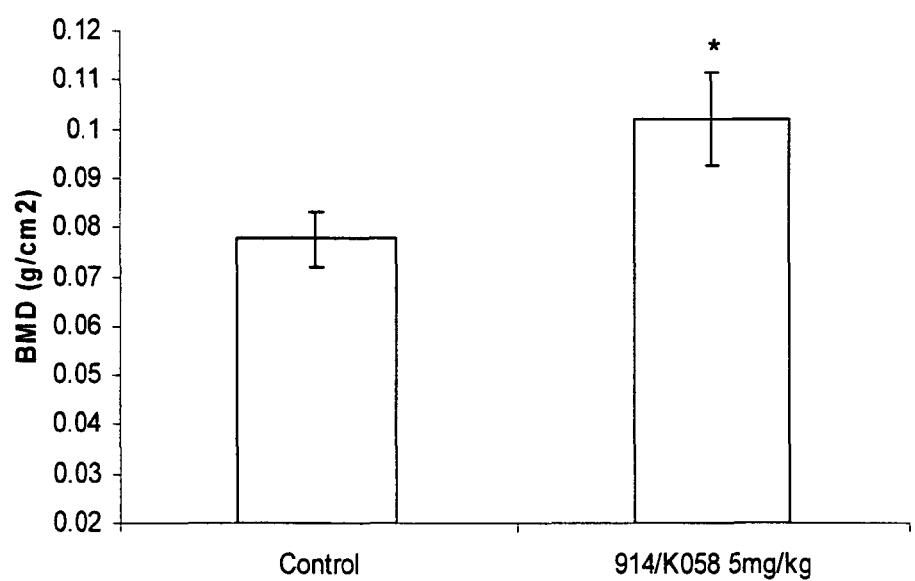

FIG. 15: K058 promotes PBM in immature rats. BMD was measured by DEXA in excised bones. Growing female rats treated with 5 mg/kg K058 was compared with vehicle (control) treated rats. BMD in femur shaft is shown (*—P<0.001, —P<0.01, *—P<0.05).

Figure 16:
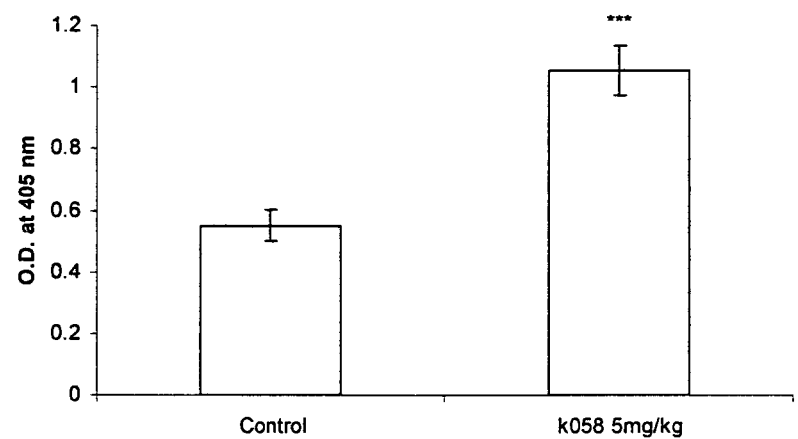
Figure 16:
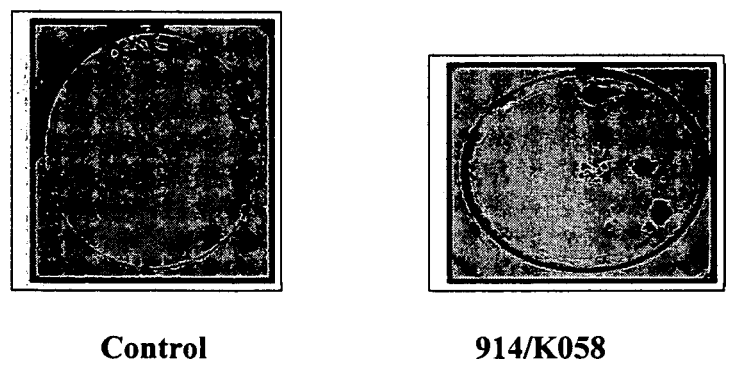
Figure 16:
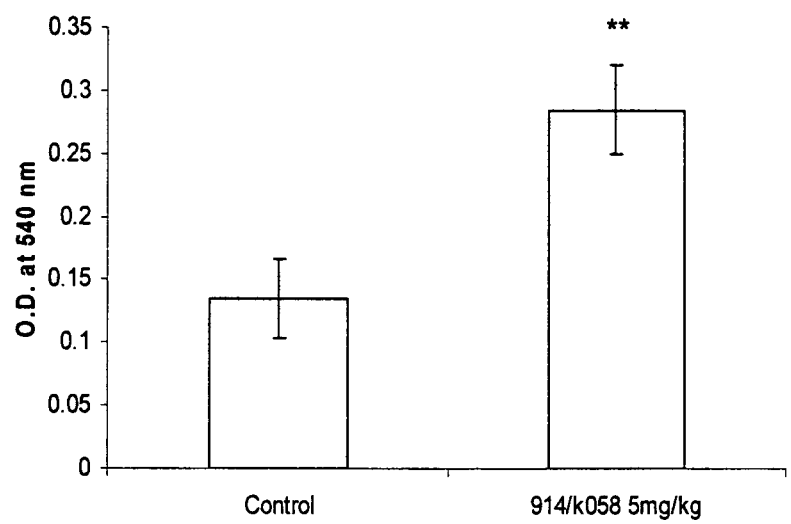

FIG. 16: K058 promotes osteoprogenitor cells in immature rats. BMCs from growing female rats treated with 5 mg/kg K058 for 30 days was compared with vehicle (control) treated rats. (A) Alkaline phosphatase assay, (B) photomicrographs of alizarin red-S stained cells and (C) quantification of alizarin red-S stain after extraction (*—P<0.001, —P<0.01, *—P<0.05).

FIG. 17: K012 reduces Ovx-induced bone loss in rats. BMD was measured by DEXA in excised bones. Ovx rats treated with 1.0&5.0 mg/kg K012 for 90 days were compared with Ovx and sham operated rats treated with vehicle (control). (A) Femur neck, (B) tibia global, (C) tibia head, (D) tibio-fibular separation point (E) lumber vertebra global, and (F) Second lumber vertebra (*—P<0.001, —P<0.01, *—P<0.05 when compared with the BMD of sham. a—P<0.001, b—P<0.01, c—P<0.05 when compared with the BMD of ovx control).

Figure 18:
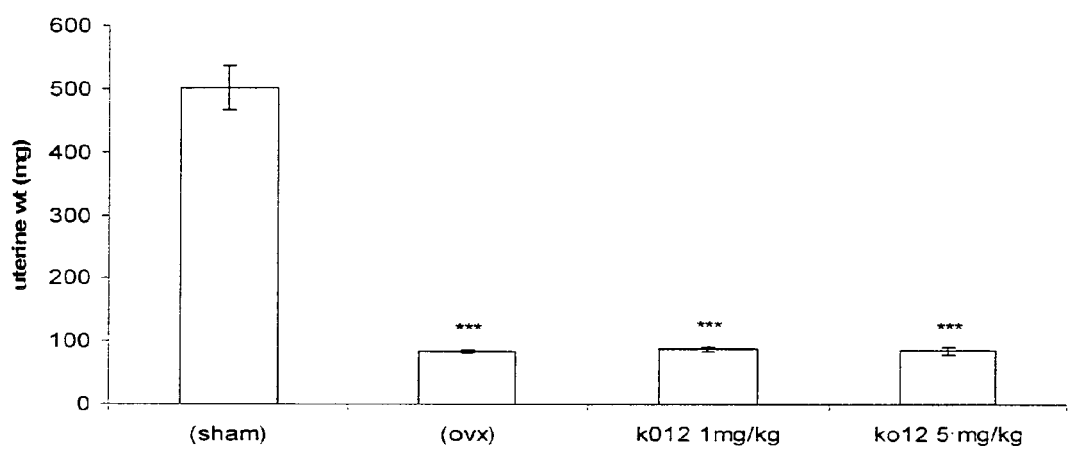

FIG. 18: K012 is not estrogenic in rats at uterine level. Uterine wt of 1.0&5.0 mg/kg b.w. K012 treated rats for 90 days was compared with uterine wt. of control sham and ovx rats. (*—P<0.001, —P<0.01, *—P<0.05 when compared with uterine wt of sham control rats, c—P<0.001, b—P<0.01, a—P<0.05 when compared with uterine wt of ovx rats).

DETAILED DESCRIPTION OF THE INVENTION

Accordingly the present invention provides a flavonol compound of general formula 1 wherein R1 and R2 is selected from a group consisting of H, OH.

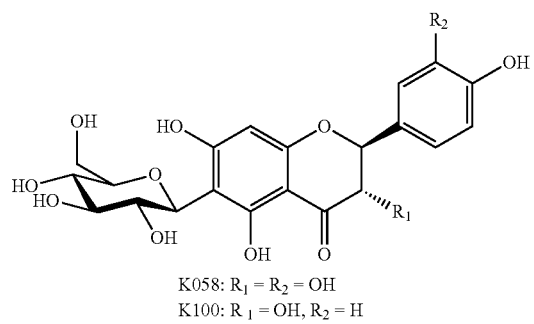

K058: $R_1 = R_2 = OH$
K100: $R_1 = OH, R_2 = H$

In an embodiment of the present invention wherein the compounds of general formula 1 are isolated from *Ulmus wallichiana*.

In another embodiment of the present invention wherein the compounds are useful for the treatment of bone disorders.

Accordingly the present invention provides a bioactive extract/fraction from *Ulmus wallichiana* useful for the management or prevention or treatment of bone disorders wherein the said extract/fraction comprising the marker compounds of general formula 2,

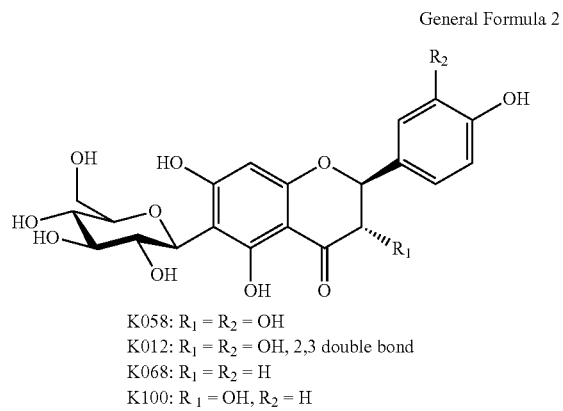

General Formula 2

K058: $R_1 = R_2 = OH$
K012: $R_1 = R_2 = OH$, 2,3 double bond
K068: $R_1 = R_2 = H$
K100: $R_1 = OH, R_2 = H$ Wherein the marker compounds K012, K058, K068, K100 ranges 6.7-12%, 1.7-4.5%, 0.6-1.2%, 1.7-4.5% respectively.

In an embodiment of the present invention wherein, the extract may be obtained from alcoholic extraction of *Ulmus wallichiana* comprising the marker compounds K012 (6.7-9%), K058 (3.3-4.5%), K068 (0.6-0.7%), K100 (1.7-2.6%).

In another embodiment of the present invention wherein acetone soluble fraction obtained from alcoholic extract comprising the marker compounds K012 (7.9-12%), K058 (1.7-3.0%), K068 (0.7-1.2%) and K100 (2.5-4.5%).

In yet another embodiment of the present invention wherein the alcoholic fraction/acetone soluble fraction is having bone sparing action under estrogen deficiency.

In still another embodiment of the present invention wherein the alcoholic fraction enhances attainment of PBM by increasing osteoprogenitor cells in the bone marrow.

In an embodiment of the present invention wherein the bioactive extract/fraction may be obtained from the plant parts selected from stem bark, twigs of *Ulmus wallichiana*.

The bioactive extract/fraction obtained from *Ulmus wallichiana* or its marker compounds of general formula 1, individually or in combination thereof, is used in the management or prevention or treatment of bone disorders.

The effective dose of alcohalic extract may be ranging between 500-750 mg/kg and acetone soluble fraction ranging between 25 mg/kg to 100 mg/kg.

General formula 2

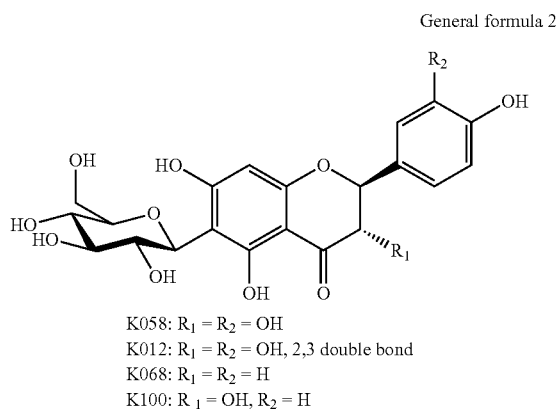

K058: $R_1 = R_2 = OH$
K012: $R_1 = R_2 = OH$, 2,3 double bond
K068: $R_1 = R_2 = H$
K100: $R_1 = OH$, $R_2 = H$ The pharmaceutically acceptable salts of general formula 2 may comprise of salts of sodium salt, potassium salt, calcium salt, oxalate, fumerate, succinate and tartarate.

The compounds of formula 2, K012, K058, K068, K100 exhibited 70 to 100% increase in ALP activity compared with control (vehicle) (FIG. 6) in calvarial osteoblasts treated at a concentration ranging between 0.1 nM to 1.0 μM.

The compounds of formula 2, were found to increase nascent calcium deposition by 10 to 25% in osteoblasts treated with K012, K058, K068, and K100, compared with control (vehicle) (FIGS. 7A & B).

The compounds of formula 1, enhance mineralization of BMCs, which is required for their osteogenic action in the skeletal growth and maintenance.

The compounds of formula 1 can be used in combination in the ratios ranging between 0.25-1.0 (K068): 1.0-5.0 (K100): 2.5-7.5 (K058): 5.0-12.5 (K012).

The compounds of formula 2, K012, K058, promoted osteoblast proliferation, differentiation and mineralization.

The compounds of formula 2, K068, and K100, promoted osteoblast differentiation, mineralization and have anti-adipogenic activity in 3T3 L1 cell line.

The compounds of formula 1, K058 exerts osteogenic action by upregulating synthesis of various genes that promote osteoblast functions and inhibiting osteoclast function.

The compounds of formula 1, K058 stimulated BrdU incorporation (a measure of cellular proliferation) of semi-confluent cultures of calvarial osteoblasts by 25 to 75% at a concentration ranging between from 10 nM to 1.0 μM (FIG. 8).

The compounds of formula 1, K058 exerts osteogenic action by up regulating synthesis of various genes that promote osteoblast functions and inhibiting osteoclast function.

Accordingly the present invention provides a pharmaceutical composition comprising an effective amount of bioactive extract/fraction from *Ulmus wallichiana* or its marker compounds of general formula 2, individually or in combination thereof, optionally along with one or more the pharmaceutically acceptable additives, carriers and diluents.

In an embodiment of the invention wherein the composition comprising; a compound selected from a group consisting of K012, K058, K068 and K100 represented by the general formula 2 individually or in combination thereof optionally along with one or more the pharmaceutically acceptable additives, carriers and diluents.

In another embodiment of the invention wherein the diluents used may be selected from the group consisting of starch, lactose, dicalcium phosphate.

In an embodiment of the invention wherein the pharmaceutically acceptable additive in the form of a lubricant may be selected from the group comprising of talc, magnesium stearate, calcium stearate or steorotes, solid polyethylene glycols, sodium lauryl sulphate or any other ingredient of the similar nature alone or in a suitable combination.

In yet another embodiment of the invention wherein the dosage of the said composition is administered at a unit dose of at least 500- to 750 mg/Kg body weight for alcoholic extract and 25- to 100 mg/Kg body weight for acetone soluble fraction.

In an embodiment of the invention wherein the alcoholic extract (C002) is derived from the *Ulmus wallichiana* having bone sparing action under estrogen deficiency, having no estrogen antagonistic action at the uterine level, enhancing attainment of PBM by increasing osteoprogenitor cells in the bone marrow in developing female rats.

Method of treating bone disorders in a subject, wherein the said method comprising the step of administering to the subject in need of a pharmaceutical composition.

In still another embodiment of the invention the composition may be administered by oral, intravenous, subcutaneous, intra-peritoneal or intramuscular route.

Accordingly the present invention provides a process for the preparation of the extract/fraction and the compounds from *Ulmus wallichiana*, wherein the process comprises:
(a) procuring the plant *Ulmus wallichiana*,
(b) powdering of the plant material,
(c) extracting the powdered plant material with protic solvent at room temperature,
(d) filtering the extract,
(e) concentrating the extract under reduced pressure,
(f) triturating the extract with hexane to remove the non-polar constituents,
(g) drying the residue under vacuum to obtain free flowing powder to give the desired extract,
(h) dissolving the extract obtained in step (g) in water,
(i) precipitating the aqueous extract by addition of n-butanol,
(j) filtering the white precipitate to obtain K058,
(k) crystallizing the compound with mixture of methanol and ethyl acetate,
(l) filtering the compound,
(m) drying the compound to obtain K058 in free flowing white powdered form,
(n) concentrating the filtrate and trituration with acetone
(o) isolating the compounds K012, K068, K100 from the acetone soluble fraction by conventional chromatographic methods, (p) quantification of K058, K012, K068, K100 in extract and in acetone soluble fraction.

In an embodiment of the invention wherein the alcohol used for extraction is selected from the group consisting of methanol, ethanol, propanol or their suitable combination thereof.

In another embodiment of the invention wherein the solvents used for trituration may be selected from a group consisting acetone, ethyl methyl ketone, dichloromethane, chloroform, ethyl acetate, methanol or a suitable combination thereof.

The present invention provides a process for the extraction, fractionation and isolation of pure compounds from natural source for the prevention or treatment of symptoms of various medical indications associated with estrogen dependent or independent diseases or syndromes caused in humans and/or animals.

The process for the preparation of extract from *Ulmus wallichiana* involves extraction of the plant material with alcohol, removing fatty nonpolar constituents by trituration with hexane.

The extract thus obtained is useful for use as nutritional product, dietary supplement or pharmaceutical composition, and may be prepared in any dosage form suitable for oral administration.

The process for the isolation of the active principle from *Ulmus wallichiana* extract involve, dissolving the extract in water and precipitating the compound by n-butanol. Alternatively, the compound obtained from the process may be derived from an aqueous-based solution. Active compound thus obtained is useful for use as nutritional product, dietary supplement or pharmaceutical composition, and may be prepared in any dosage form suitable for oral administration.

Methods of preventing or treating disorders or disease conditions mentioned herein comprise administering to an individual human being or any other mammal or any other animal in need of such treatment a therapeutically effective amount of one or more of the agents of this invention.

The dosage regimen and the mode of administration of the agents of this invention or a pharmaceutically acceptable salt or a pharmaceutically acceptable composition thereof with one or more of the pharmaceutically acceptable carriers, excipients etc. will vary according to the type of disorder or disease conditions described herein and will be subject to the judgment of the medical practitioner involved.

The agent of this invention or a pharmaceutically acceptable salt or a pharmaceutically acceptable composition thereof with one or more of the pharmaceutically acceptable carriers, excipients etc. may be effectively administered in doses ranging from 0.1 mg to 5000 mg, more preferably in doses ranging from 0.5 to 1000 or still more preferably in the doses ranging from 1 mg to 500 mg weekly or bi-weekly or daily or twice a day or three times a day or in still more divided doses.

Such doses may be administered by any appropriate route for example, oral, systemic, local or topical delivery for example, intravenous, intra-arterial, intra-muscular, subcutaneous, intra-peritoneal, intra-dermal, buccal, intranasal, inhalation, vaginal, rectal, transdermal or any other suitable means in any conventional liquid or solid dosage form to achieve, conventional delivery, controlled delivery or targeted delivery of the compounds of this invention or a pharmaceutically acceptable salt or a pharmaceutically acceptable composition thereof with one or more of the pharmaceutically acceptable carriers, excipients etc.

A preferred mode of administration of agents of the present invention or a pharmaceutically acceptable salt or a pharmaceutically acceptable composition there of is oral. Oral compositions will generally comprise of agents of the present invention or a pharmaceutically acceptable composition thereof and one or more of the pharmaceutically acceptable excipients.

The oral compositions such as tablets, pills, capsules, powders, granules, and the likes may contain any of the following pharmaceutically acceptable excipients:

1. a diluent such as lactose, mannitol, sorbitol, microcrystalline cellulose, sucrose, sodium citrate, dicalcium phosphate, or any other ingredient of the similar nature alone or in a suitable combination thereof;
2. a binder such as gum tragacanth, gum acacia, methyl cellulose, gelatin, polyvinyl pyrrolidone, starch or any other ingredient of the similar nature alone or in a suitable combination thereof;
3. a disintegrating agent such as agar-agar, calcium carbonate, sodium carbonate, silicates, alginic acid, corn starch, potato tapioca starch, primogel or any other ingredient of the similar nature alone or in a suitable combination thereof;
4. a lubricant such as magnesium stearate, calcium stearate or steorotes, talc, solid polyethylene glycols, sodium lauryl sulphate or any other ingredient of the similar nature alone or in a suitable combination thereof;
5. a glidant such as colloidal silicon dioxide or any other ingredient of the similar nature alone or in a suitable combination thereof;
6. a sweetening agent such as sucrose, saccharin or any other ingredient of the similar nature alone or in a suitable combination thereof;
7. a flavoring agent such as peppermint, methyl salicylate, orange flavor, vanilla flavor, or any other pharmaceutically acceptable flavor alone or in a suitable combination thereof;
8. wetting agents such as cetyl alcohol, glyceryl monostearate or any other pharmaceutically acceptable flavor alone or in a suitable combination thereof;
9. absorbents such as kaolin, bentonite clay or any other pharmaceutically acceptable flavor alone or in a suitable combination thereof;
10. solution retarding agents such as wax, paraffin or any other pharmaceutically acceptable flavor alone or in a suitable combination thereof.

Therefore, the present invention seeks to overcome prior problems associated with the cure and the management associated with estrogen dependent or independent diseases or syndromes or disorders preferably in the prevention or treatment of estrogen dependent or independent diseases caused in humans and animals and more particularly the bone health disorders and syndromes. The invention also seeks to promote peak bone mass achievement during skeletal growth as occurs in adolescence. The crude extract and the acetone soluble fraction and the pure compounds K012, K058, K068 and K100 from *Ulmus wallichiana* described in the present invention are useful in the management, prevention treatment, and cure of estrogen dependent or independent diseases or syndromes or disorders preferably in the prevention or treatment of estrogen dependent or independent diseases or syndromes or disorders caused in humans and animals, and attainment of PBM during skeletal growth and health in humans and animals.

One of the main object of the present invention is to provide the crude extract derived from *Ulmus wallichiana* in pharmaceutically acceptable form in order to enhance its application potential for the management or prevention or treatment or cure of estrogen dependent or independent diseases or syndromes or disorders preferably in the prevention or treatment of estrogen dependent or independent diseases or syndromes or disorders caused in humans and animals, and attainment of PBM during skeletal growth and health in humans and animals.

Another object of the present invention is to provide the acetone soluble fraction derived from *Ulmus wallichiana* in pharmaceutically acceptable form in order to enhance its application potential for the management or prevention or treatment or cure of estrogen dependent or independent diseases or syndromes or disorders preferably in the prevention or treatment of estrogen dependent or independent diseases or syndromes or disorders caused in humans and animals, and attainment of PBM during skeletal growth and health in humans and animals.

Still another object of the invention is to provide individual pure compounds derived from *Ulmus wallichiana* in pharmaceutically acceptable form in order to enhance their application potential for the management or prevention or treatment or cure of estrogen dependent or independent diseases or syndromes or disorders preferably in the prevention or treatment of estrogen dependent or independent diseases or syndromes or disorders caused in humans and animals, and attainment of PBM during skeletal growth and health in humans and animals.

Yet another object of the invention is to provide a cocktail of two or more than two pure compounds derived from *Ulmus wallichiana*, in a suitable ratio or ratios, in pharmaceutically acceptable form in order to enhance their application potential for the management or prevention or treatment or cure of estrogen dependent or independent diseases or syndromes or disorders preferably in the prevention or treatment of estrogen dependent or independent diseases or syndromes or disorders caused in humans and animals, and attainment of PBM during skeletal growth and health in humans and animals.

Accordingly the present invention provides a crude extract or acetone soluble fraction or individual pure compounds or cocktail of suitable ratio or ratios of two or more than two pure compounds derived from *Ulmus wallichiana* in pharmaceutically acceptable form to enhance their application potential for the management or prevention or treatment or cure of estrogen dependent or independent diseases or syndromes or disorders preferably in the prevention or treatment of estrogen dependent or independent diseases or syndromes or disorders caused in humans and animals, and attainment of PBM during skeletal growth and health in humans and animals, by the process and the methods described in the present invention.

In an embodiment of the invention the crude extract useful for management or prevention or treatment or cure of estrogen dependent or independent diseases or syndromes or disorders preferably in the prevention or treatment of estrogen dependent or independent diseases or syndromes or disorders caused in humans and animals, and attainment of PBM during skeletal growth and health in humans and animals, is prepared from the stem bark and twigs of the plant *Ulmus wallichiana*.

In another embodiment of the invention the acetone soluble fraction, useful for management or prevention or treatment or cure of estrogen dependent or independent diseases or syndromes or disorders preferably in the prevention or treatment of estrogen dependent or independent diseases or syndromes or disorders preferably in the prevention or treatment of estrogen dependent or independent diseases or syndromes or disorders caused in humans and animals, and attainment of PBM during skeletal growth and health in humans and animals, is prepared from the crude extract is prepared from the stem bark and twigs of the plant *Ulmus wallichiana*.

In yet another embodiment of the invention the individual pure compounds, useful for management or prevention or treatment or cure of estrogen dependent or independent diseases or syndromes or disorders preferably in the prevention or treatment of estrogen dependent or independent diseases or syndromes or disorders preferably in the prevention or treatment of estrogen dependent or independent diseases or syndromes or disorders caused in humans and animals, and attainment of PBM during skeletal growth and health in humans and animals, are derived from the crude extract or acetone soluble fraction of the stem bark and twigs of the plant *Ulmus wallichiana*.

In yet another embodiment of the invention the ratios and absolute concentration of the individual pure compounds in the crude extract or acetone soluble fraction of *Ulmus wallichiana* and useful for management or prevention or treatment or cure of estrogen dependent or independent diseases or syndromes or disorders preferably in the prevention or treatment of estrogen dependent or independent diseases or syndromes or disorders caused in humans and animals, and attainment of PBM during skeletal growth and health in humans and animals, have been derived using HPLC based method of quantification.

In yet another embodiment of the invention the individual pure compounds in the crude extract or acetone soluble fraction of *Ulmus wallichiana* were evaluated in vitro and in vivo using well established protocols and procedures to establish and demonstrate their usefulness in management or prevention or treatment or cure of estrogen dependent or independent diseases or syndromes or disorders preferably in the prevention or treatment of estrogen dependent or independent diseases or syndromes or disorders caused in humans and animals, and attainment of PBM during skeletal growth and health in humans and animals.

The following examples are given by way of explanation and should not construed the scope of the present invention.

EXAMPLES

1. Extraction from Stem Bark

Powdered stem bark of *Ulmus wallichiana* (Plant code No. 914, 5 kg) were placed in glass percolator with ethanol (20 L) and are allowed to stand at room temperature for about 16 hours (overnight). The percolate was collected. This process of extraction was repeated for four times. The combined extract was filtered, concentrated at 45° C.; weight of extract obtained 660 g (13.2%, 914-0002).

2. Extraction from Twigs

Powdered twigs of *Ulmus wallichiana* (Plant code No. 4669, 4 kg) were placed in glass percolator with ethanol (18 L) and are allowed to stand at room temperature for about 16 hours (overnight). The percolate was collected. This process of extraction was repeated for four times. The combined extract was filtered, concentrated at 45° C.; weight of extract obtained 350 g (8.7%, C002).

3. Fractionation

Ethanolic extract (914-0002, 100 g) was triturated with hexane (200 ml×5). The hexane soluble fraction was then concentrated under the reduced pressure at 40° C., weight of hexane fraction obtained 10 g (10%, F003). Residue obtained after triturating with hexane was then dissolved in water (500 ml), precipitated with addition of n-butanol (500 ml). Solid obtained filtered, washed with distilled water. The pure compound was obtained by crystallization with mixture of methanol and ethyl acetate, obtained 2.6 g (2.6%, K058). The filtrate was concentrated using rotavapour at 45° C. The residue was triturated with acetone (200 ml×4). The combined acetone soluble fraction was concentrated under reduced pressure. Weight of acetone soluble fraction obtained 69.0 g (F004) and acetone insoluble fraction obtained 18.4 g, (F005).

A schematic diagram showing extraction, fractionation and isolation strategies from *Ulmus wallichiana* is represented in FIG. 1.

FIG. 1: Flow diagram showing extraction, fractionation and isolation of crude extract and pure fractions from *Ulmus wallichiana* stem bark.

4. Isolation of Compounds from Acetone Soluble Fraction (F004) of *Ulmus wallichiana*

Chromatography of acetone soluble fraction (69.0 g) over silica gel (230-400, mesh), employing mixture of $CHCl_3$ to $CHCl_3$: MeOH ((5%) aq), afforded K068 (0.200 g. (0.2%) using $CHCl_3$: (5%) aq MeOH (93:7) as eluent, K100 (0.20 g., 0.20%) using $CHCl_3$: (5%) aq MeOH (90:10) as eluent and K012 (2.5 g. 2.5%) using $CHCl_3$: (5%) aq MeOH (87:13) as eluent. These compounds were characterized from detailed spectroscopic studies. K058 and K100 are new compounds and K068 and K012 are known compounds.

Physical and Spectral Data of Isolated Compounds

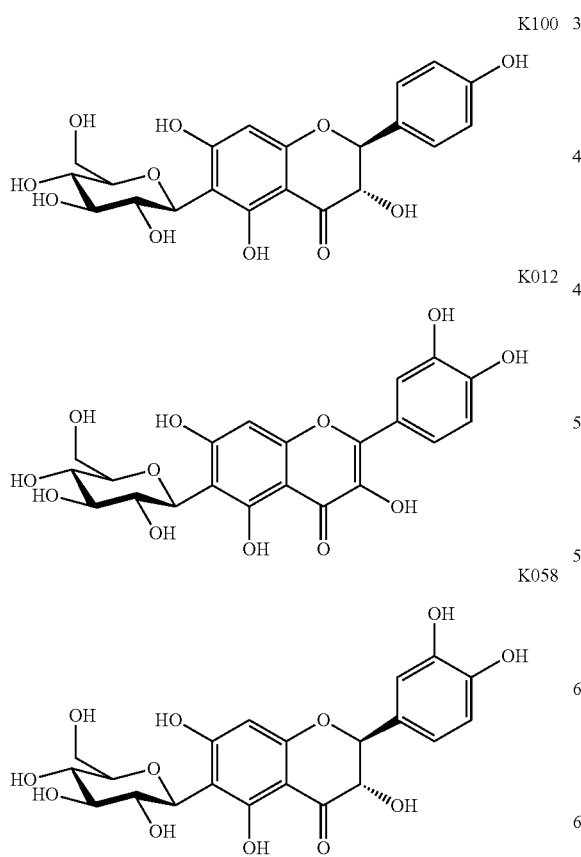

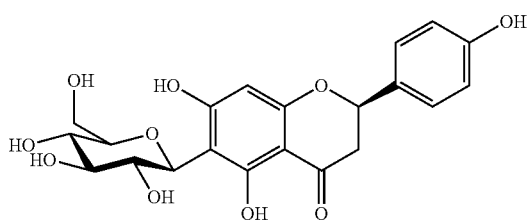

5. Characterization of K012, K058, K068 and K100

K058: (2S,3S)-(+)-3',4',5,7-tetrahydroxydihydroflavonol-6-C-β-D-glucopyranoside Yield: 2.6 g. (2.6%); amorphous; UV $\lambda_{max}$ MeOH: 290, 327 nm; $[\alpha]_D^{25}$+1.33° (c, 0.098; MeOH);). CD (MeOH) $\Delta\epsilon_{304}$+36.27 $\Delta\epsilon_{332}$–12.21. FAB-MS: m/z 467 $[M+1]^+$; $C_{21}H_{22}O_{12}$; $^1$H NMR: (DMSO-$d_6$, 300 MHz) δ: 4.92 (1H, d, J=10.1 Hz, H-2), 4.49 (1H, m, H-3), 5.92 (1H, s, H-8, 6.87 (1H, s, H-5'), 6.74 (2H, s, H-2', 6'), 4.87 (1H, m, H-1" along with OH signal), 3.14 (2H, m, H-2", 5"), 3.48 (1H, m, H-3"), 3.67 (1H, m, H-4"), 4.01 (1H, m, H-6"a), 4-0.47 (1H, m, H-6"b), 12.48 (1H, s, OH-5), 9.11 (1H, s, OH-3), 9.05 (1H, s, OH-3'), 4.84 (1H, brs, OH), 4.62 (1H, brs, OH). $^{13}$C NMR: (DMSO-$d_6$, 75 MHz) δ: 83.0 (C-2), 71.63 (C-3), 197.9 (C-4), 162.6 (C-5), 106.0 (C-6), 166.0 (C-7), 94.8 (C-8), 161.3 (C-9), 100.2 (C-10), 128.0 (C-1'), 115.3 (C-2'), 145.8 (C-3'), 145.0 (C-4'), 115.3 (C-5'), 119.4 (C-6'), 72.9 (C-1"), 70.7 (C-2"), 79.1 (C-3"), 70.3 (C-4"), 81.5 (C-5"), 61.6 (C-6").

K012 (6-Glucopyranosyl-3,3',4',5,7-pentahydroxyflavone)

Yield: 2.5 g. (2.5%); amorphous; UV $\lambda_{max}$ MeOH: ---- nm; $[\alpha]_D^{25}$+9.79° (c, 0.0612; DMSO); FAB-MS: m/z 465 $[M+1]^+$; $C_{21}H_{20}O_{12}$; $^1$H NMR: (DMSO-$d_6$, 300 MHz) δ 6.48 (1H, s, H-8), 7.65 (1H, d, J=2.1 Hz, H-2'), 6.88 (1H, d, J=8.5 Hz, H-5'), 7.54 (1H, dd, J=8.5, 2.1 Hz, H-6'), 4.59 (1H, d, J=9.6 Hz, H-1"), and other sugar protons are at 4.05-3.20 (5H, m, H-2"-6"), 13.06 (1H, s, OH-12), 9.35 (1H, s, OH-3). $^{13}$C NMR: (DMSO-$d_6$, 75 MHz) δ: 144.2 (C-2), 134.7 (C-3), 175.2 (C-4), 159.0 (C-5), 107.2 (C-6), 162.2 (C-7), 92.2 (C-8), 154.2 (C-9), 101.8 (C-10), 121.0 (C-1'), 114.7 (C-2'), 145.7 (C-3'), 146.8 (C-4'), 114.1 (C-5'), 119.2"(C-6'), 72.2 (C-1"), 69.7 (C-2"), 78.1 (C-3"), 69.3 (C-4"), 80.7 (C-5"), 60.6 (C-6").

K068 (6-Glucopyranosyl-4',5,7-trihydroxyflavanone)

Yield: 0.200 g. (0.2%); mp: 195-196° C.; UV $\lambda_{max}$ MeOH: 292, 328 nm; $[\alpha]_D^{25}$+29.32° (c, 0.133; MeOH); FAB-MS: m/z 435 $[M+1]^+$; $C_{21}H_{22}O_{10}$; $^1$H NMR: ($CD_3OD$, 300 MHz) δ: 5.35 (1H, dd, J=12.4, 2.3 Hz, H-2), 2.75 (1H, dd, J=2.3, 17.1 Hz, H-3a), 3.14 (1H, dd, J=12.4, 17.1 Hz, H-3b), 5.98 (1H, s, H-8), 7.32 (2H, d, J=8.4 Hz, H-2', 6'), 6.82 (2H, d, H-3',5'), 4.79 (1H, d, J=9.4 Hz, H-1"), 4.11 (1H, m, H-2"), 3.45 (1H, m, H-3"), 3.30 (2H, m, H-4",5"), 3.86 (1H, dd, J=2.2, 12.3 Hz, J=5.2, 12.3 Hz, H-6"b), 3.73 (1H, m, H-6"a); $^{13}$C NMR: ($CD_3OD$, 75 MHz) δ: 82.9 (C-2), 44.0 (C-3), 198.2 (C-4), 164.3 (C-5), 106.1 (C-6), 167.4 (C-7), 96.5 (C-8), 159.1 (C-9), 103.4 (C-10), 131.0 (C-1'), 129.1 (C-2'), 116.1 (C-3'), 164.6 (C-4'), 116.1 (C-5'), 129.1 (C-6'), 75.3 (C-1''), 72.7 (C-2''), 80.2 (C-3''), 71.9 (C-4''), 80.0 (C-5''), 63 (C-6'').

K100: (2S,3S)-(+)-4',5,7-trihydroxydihydroflavonol-6-C-β-D-glucopyranoside

Yield: 0.20 g. (0.20%); amorphous; UV $\lambda_{max}$ MeOH: 296, 334 nm; $[\alpha]_D^{25}$+48.69° (c, 0.115; MeOH); CD (MeOH) $\Delta\epsilon_{299}$+27.35 $\Delta\epsilon_{328}$-15.56. FAB-MS: m/z 451 [M+1]$^+$; $C_{21}H_{22}O_{11}$; $^1$H NMR: (CD$_3$OD, 300 MHz) δ: 4.95 (1H, d, J=11.3 Hz, H-2), 4.55 (1H, d, J=11.3 Hz, H-3), 5.95 (1H, s, H-8), 7.34 (2H, d, J=8.5 Hz, H-2',6'), 6.83 (21-1, d, J=8.5 Hz, H-3',5'), 4.82 (1H, m, H-1'' along with OH signal), 4.13 (1H, t, J=9.1 Hz, H-2''), 3.86 (1H, dd, J=2.1, 12.3 Hz, H-6''a), 3.71 (1H, dd, J=4.9, 12.3 Hz, H-6''b), 3.45-3.35 (3H, m, H-3'',4'',5''), $^{13}$C NMR: (CD$_3$OD, 75 MHz), δ: 85.0 (C-2), 72 (C-3), 198.9 (C-4), 163.9 (C-5), 106.3 (C-6), 167.4 (C-7), 96.4 (C-8), 159.2 (C-9), 101.8 (C-10), 129.2 (C-1'), 130.4 (C-2'), 116.2 (C-3'), 164.1 (C-4'), 116.2 (C-5'), 130.4 (C-6'), 75.2 (C-1''), 72.6 (C-2''), 80.2 (C-3''), 71.9 (C-4''), 82.6 (C-5''), 62.9 (C-6'').

6. Quantification of K058, K012, K068, K100 in Crude Extract and in Acetone Soluble Fraction HPLC-PDA based analytical method was employed for the absolute quantification, of K012, K058, K068, K100 in the crude extract and acetone soluble fraction. The analysis was performed on C-18 column using Methanol:Water as the mobile phase at a flow rate of 0.5 ml per minute. The individual markers K012, K058, K068, K100 appeared at 15±0.8, 8.3±0.8, 14.3±0.8, and 10±0.8 minutes respectively in the chromatogram. Accuracy and precision of the individual pure markers K058, K012, K068, K100 were established by intra and inter-day analysis in the concentration range of 0.5-16 μg/ml with a correlation coefficient of 0.99 or better. Crude extracts and Acetone soluble fraction were analyzed utilizing the above method and the absolute concentration of these four marker components in crude extracts and acetone soluble fractions were extrapolated from the linearity graph. K012, K058, K068, K100 were found to be present in the concentration range of 6.7-9%, 3.3-4.5%, 0.6-0.7% and 1.7-2.6% respectively, in the crude extract and in the range of 7.9-12%, 1.7-3.0%, 0.7-1.2% and 2.5-4.5% respectively in the acetone soluble fraction.

7. Biological Evaluation

The plant extracts and pure compound of the present invention were evaluated for the use of estrogen dependent or independent diseases or syndromes or disorders preferably in the prevention or treatment of estrogen dependent or independent diseases or syndromes or disorders caused in humans and animals, and achievement of PBM during skeletal growth and health in mammals. Detailed procedures for the evaluation of the ethanolic extract of stem bark and isolated compounds of the present invention are described subsequently. The activity testing illustrated in the following examples should, however, not be construed to limit the scope of invention.

7.1 Test Procedure for the Determination of Osteogenic or Bone Forming Activity

Test solutions of the test extracts of the present invention are prepared in dimethyl sulfoxide (a stock of 10 mM) and diluted in culture medium at concentrations 1 nM and 100 nM for evaluation of bone forming activity in vitro. In control experiments, equal concentration of DMSO was used in lieu of the test agent.

7.2 Osteoblast Cell Culture

Osteoblasts arise from pluripotent mesenchymal stem cells. One of the richest sources of pre-osteoblasts is the calvaria of newborn rat or mouse. Osteoblasts are also present in the bone marrow. During the course of culture, pre-osteoblasts undergo three characteristic stages of osteoblasts with the expression of stage specific genes. These are:

Proliferation & differentiation: Days 1-12
Genes—Alkaline phosphatase, Collagen-I, osteocalcin etc.
Extra-cellular matrix maturation:
Days 12-18
Genes—Osteocalcin, Osteopontin, Fibronectin
Mineralization: Days 14-35
Feature—Calcification (nodule formation)

The Ethanolic extract was not included in in vitro studies as it was found to precipitate in culture medium even at the 0.0025% dilution, most probably due to the abundance of non-polar groups. Therefore, we tested the pure compounds on osteoblasts and pre-adipocytes.

7.3 Treatment of Crude Extract (C002) of *Ulmus wallichiana* in Ovariectomized Sprague Dawley Rats Ethanolic extracts of C002 at the doses of 500-& 750 mg/kg body weight were given daily by oral route to Sprague Dawley (180-200 g) rats after bilateral ovariectomy (Ovx). This is the most widely used animal model for osteopenia (bone loss) mimicking human condition of post-menopausal bone loss. The extract was given in gum acacia (vehicle). Sham operated rats and Ovx rats were used as controls and given only gum acacia. Each group consisted of 10 rats and the groups were as follows: sham intact, Ovx, Ovx+500 mg/kg extract and Ovx+750 mg/kg extract. Treatment started 24 h after the surgery and continued for 90 days. After 90 days, the rats were first acclimatized and then kept in metabolic cages with no food but only water for 24 h to collect urine samples. After 24 h, rats were returned to the cages with food and water ad libitum with oral administration of the extract as before foe an additional 24 hour. Rats were then euthanized and autopsied to collect blood, bones (tibia, femur, L1-L4 vertebrae) and uterus.

7.4 Measurement of Bone Mineral Density (BMD)

Bone mineral density of femur (global, head, neck), tibia (global, head, tibio-fibular separation point) and lumber vertebra (LV1, LV2, LV3, LV4) was determined by DEXA.

7.5 Treatment of C002 and F004 (Fraction of C002) in Growing Sprague Dawley Rats 21 days old female Sprague Dawley rats were divided into three groups, each group consisted of 10 rats; control (vehicle treated), 750 mg/kg C002 crude extract, and 50 mg/kg 914/F004. Vehicle or treatments were given daily by oral route in gum acacia for 30 days. After completion of 30 days the rats were euthanized and there bones (femur, tibia, L1-L4 vertebra) were collected.

7.6 Measurement of Bone Mineral Density (BMD)

Bone Mineral Density of Femur (Global, head, neck), tibia (global, head, tibio-fibular separation point) and lumber vertebra (LV1, LV2, LV3, LV4) was determined by DEXA.

7.7 Ex-Vivo Cultures of Bone Marrow for ALP (Alkaline Phosphatase) Quantitation and In Vitro Mineralization from C002 Treated Immature Rats Right femur of control and C002 treated rats were collected aseptically in PBS during autopsy from the rats. Soft tissue was removed, and the ends of the femur was clipped off using sterile scissors, a hole was created in the knee joint end of each bone with a needle, and the marrow was flushed out from the shaft with control medium (CM) which consisted of α-MEM supplemented with 10% fetal calf serum, 100 U/ml penicillin, 100 U/ml streptomycin (Sigma, Chemical Co., St. Louis, Mo., USA). The cells were suspended in this medium, and the suspensions were spun down at 800 rpm for 5 min. Cells were resuspended in fresh CM and counted using a haemocytometer. 100000 and 200000 cells/well were cultured in 48-well and 12-well plates respectively and in a humidified atmosphere, with 5% $CO_2$, at 37° C. in CM supplemented with 10 mM-β-glycerophosphate, 50 μg/ml L-ascorbic acid and $10^{-8}$M dexamethasone. This medium was replaced every other day (John et al. 2002; Connolly, 1995; Gebhart and Lane. 1991; Gurpinar et al. 2003; Lan and Wang. 2003). The cells were maintained for 9 days for ALP activity. ALP activity was determined as described by Akiyama et al. with modifications. Briefly, cells were washed once with PBS, then, ALP activity was measured by adding ALP buffer (1 M diethanolamine, 0.5 mM $MgCl_2$, 1 mg/ml PNPP, pH 9.0), incubating in 37° C., and absorbance (405 nm) was read using a microplate spectrophotometer. Statistical significance was determined by paired two-tailed Student's t-tests.

For in vitro mineralization, cells were maintained as described above for 21 days followed by fixation (4% HCHO in PBS for 20 min). Samples were then rinsed with nanopure water and stained for 10 min with 40 mM alizarin red-S, pH 4.2, at room temperature. Samples were rinsed five times with water. Photomicrographs of the stained wells were taken. Subsequently, alizarin red-S stain was extracted using 10% (w/v) cetylpyridinium chloride (CPC) in 10 nM sodium phosphate, pH 7.0, for 15 min at room temperature, and the resulting solutions were read on a Microplate reader with a test wavelength of 540 nm against a reference wavelength of 620 nm.

7.8 Primary Osteoblast Cultures

Neonatal rat calvarial cell cultures are prepared as described previously (Chattopadhyay et al., Endocrinology 145:3451-62, 2004) using slight modification. Briefly, for calvarial osteoblast cultures, frontal and parietal bones from neonatal Sprague-Dawley rats (1-3 day old) were digested in 0.1% collagenase/0.1% dispase in α-MEM to obtain 5 sequential digests. The second through fifth digests are combined and grown to confluence at 37° C. and 5% $CO_2$ in air in α-MEM, supplemented with 10% fetal bovine serum (FBS), 2 mM glutamine, 100 U/ml penicillin-streptomycin, non-essential amino acid solution and sodium pyruvate.

7.9 BrdU Cell Proliferation Assay

BrdU assay is used to measure cell proliferation based on the incorporation of BrdU during DNA synthesis in proliferating cells (Chattopadhyay et al., Endocrinology 145:3451-62, 2004). Calvarial osteoblasts were seeded in 96-well plates (2000 cells/well). Cells were allowed to attach for 24 h and after that cells were starved in 0.5% FCS containing α-MEM medium followed by treatment of K058 at various concentrations for 24 hrs following which cell proliferation was determined by BrdU ELISA method as described by the manufacturer (Roche Biochemicals, Rotkreuz, Switzerland). 4 h before the completion of reaction, BrdU solution was added. BrdU incubation was carried out for 4 h, cells were fixed and denatured and subsequently treated with anti-BrdU antibody and the immune complexes were detected by the substrate reaction. Absorbance was measured at 370 nm.

7.10 Alkaline Phosphatase Activity Assay

For alkaline phosphatase (ALP) assay, osteoblasts were plated in 96-well (2000 cells/well) plates in regular growth medium. Twenty-four hours later, when the cells formed a confluent monolayer, medium was replaced with α-MEM medium supplemented with 10% FBS, 10 mM β-glycerophosphate and 50 μg/ml ascorbic acid. Treatment was given with varying concentration of the test compound K012, K058, K068 and K100 at 1 nM and 100 nM concentration. Forty-eight hours after induction, ALP activity of the osteoblasts was determined as described by Akiyama et al (Exp Cell Res 235:362-369, 1997) with slight modifications. Briefly, cells were washed once with PBS and ALP activity was measured by adding ALP buffer (1 M diethanolamine, 0.5 mM $MgCl_2$, 1 mg/ml PNPP, pH 9.0), incubating in 37° C., and absorbance (405 nm) was measured using a microplate spectrophotometer. Statistical significance was determined by paired two-tailed Student's t-tests.

7.11 In Vitro Mineralization from Calvarial Osteoblasts

Ability of cells to produce mineralized matrix is important with regard to development of materials for bone regeneration. Mineralization of extracellular matrix by osteoblasts was determined using alizarin red-S (AR-S) assay combined with cetylpyridinium chloride (CPC) extraction. (Stanford et al, J. Biol. Chem. 270:9420-9428; 1995.) Alizarin red is a dye that binds selectively to nascent calcium salts and is widely used for calcium mineral histochemistry. Cells were seeded onto a six well plate containing 10000 cells/well in culture medium supplemented with 10 mM β-glycerophosphate and 50 μg/ml ascorbic acid with test compounds K012, K058, K068 and K0100 at 1 nM and 100 nM concentration. Treatment was given for 21 days and after completion of the treatment samples were rinsed with PBS followed by fixation (4% HCHO for 20 min). Photomicrographs of the stained wells were taken. Subsequently, alizarin red-S stain was extracted using 10% (w/v) cetylpyridinium chloride (CPC) in 10 nM sodium phosphate, pH 7.0, for 15 min at room temperature, and the resulting solutions were read on a Microplate reader with a test wavelength of 540 nm against a reference wavelength of 620 nm. Mineralization nodules were also seen by Von kossa staining procedure (A. M. Chou et al. Materials Science and Engineering C 20 (2002) 77-83.) After 21 days culture, cells in tissue culture wells were washed with PBS and immersed in 5% (w/v) silver nitrate solution for 45 min. After rinsing with distilled water, they were fixed in 5% (w/v) sodium bicarbonate formalin for 8 min. Finally, they were immersed in 5% (w/v) sodium thiosulphate solution for 5 min and washed thoroughly with water for 15 min and photomicrographs were taken.

7.12 In Vitro Mineralization from Mouse Bone Marrow

Adult balb/c mice were used in this study. Bone marrow cells (BMCs) were harvested from the femurs and tibias of the animals, as described elsewhere (Maniatopoulos et al. Cell Tissue Res 1988:254:317-30.; Ishaug et al., J Biomed Mater Res 1997; 36:17-28.). Briefly, bones were aseptically excised from the hind limbs of the mice following ether euthanasia. The soft tissue was removed, and the proximal end of the femur and distal end of the tibia were clipped off using sterile scissors, a hole was created in the knee joint end of each bone with an needle, and the marrow was flushed from the shaft with control medium (CM) which consisted of α-MEM supplemented with 10% fetal calf serum, 100 U/ml penicillin, 100 U/ml streptomycin (Sigma, Chemical Co., St. Louis, Mo., USA). The cells were suspended in this medium, and the cell suspensions from all bones were combined in a centrifuge tube. The suspension was spun down at 800 rpm for 5 min. Cells were counted by using a haemocytometer. The supernatant was aspirated, and the pellet was re-suspended in fresh CM and then seeded into 12-well plates. 200000 cells/well were cultured in 12-well plates and in a humidified atmosphere, with 5% $CO_2$, at 37° C. in the same medium supplemented with 10 mM-β-glycerophosphate, 50 µg/ml L-ascorbic acid and $10^{-8}$M dexamethasone with different concentration of the test compound. This medium was replaced every other day (John et al. *Trends. Biomater. Artif. Organs* 2002:16(1):28-33.; Connolly. *Clin Orthop* 1995:313: 8-18.; Gebhart and Lane. *Acta Orthop Belg* 1991:57(2):130-43.; Gurpinar et al. *J Biomater Appl* 2003; 18(1):25-33; Lan and Wang, *Blood Substitutes. Biotechnol* 2003; 31(1):59-68.). Treatments K012, K058, K068 and K0100 at 1 nM and 100 nM concentration were given for 21 days and after completion of the treatment samples were rinsed with PBS followed by fixation (4% HCHO for 20 mM). Samples were then rinsed with nanopure water and stained for 10 min with 40 mM AR-S, pH 4.2, at room temperature. Treatment was given for 21 days and after completion of the treatment samples were rinsed with PBS followed by fixation (4% HCHO for 20 min). Photomicrographs of the stained wells were taken. Subsequently, alizarin red-S stain was extracted using 10% (w/v) CPC in 10 nM sodium phosphate, pH 7.0, for 15 mM at room temperature, and the resulting solutions were read on a Microplate reader with a test wavelength of 540 nm against a reference wavelength of 620 nm.

7.13A In Vitro Adipogenesis

3T3-L1 preadipocyte cells were cultured to confluency. Two days after the cells reached confluency was considered as day 0. At day 0, cells were treated with the induction media [10% calf serum/DMEM containing 1 µg/ml insulin, 1 µM dexamethasone and 500 µM isobutylmethylxanthine (IBMX). Two days after induction medium treatment (day 2), the cells were treated with insulin [10% calf serum/DMEM containing 1 µg/ml insulin. Full differentiation was usually achieved after 8 days from day 0. To test the effect of the test compound on the differentiation of 3T3-L1 preadipocytes to adipocytes, the test compounds K068 and K100 at 1 µM, 100 nM and 1 nm concentrations were used in different concentrations throughout differentiation (for 8 days starting from day 0). For assessment of adipogenesis the differentiated cells were fixed in 4% paraformaldehyde w/v for 20 min, washed with PBS and stained with 0.34% Oil Red 0 in 60% isopropanol for 15 minutes. Then it was washed with PBS thrice and stain was extracted with 80% isopropanol by keeping it at room temperature for 30 minutes on an orbital shaker. OD of the extracted dye was taken at 520 nm.

7.13B Reverse Transcriptase Polymerase Chain Reaction (RT-PCR)

RT-PCR was performed for assessing the expression of PPAR-γ (peroxisome proliferator-activated receptor) and adiponectin. The house keeping gene GAPDH was used as the internal control in this study. 3T3-L1 preadipocytes were cultured under differentiation condition to form adipocytes in the presence of K068 and K100 at $10^{-6}$, $10^{-7}$ and $10^{-9}$ M concentrations for 8 days. Following the culture, cellular RNA was extracted and RT-PCR performed using a kit (Fermentas) according to manufacturer's instructions. PCR was performed using the oligonucleotides listed in Table 1.

TABLE 1

Primer sequences for RT-PCR

| Gene | Sequence | Accession No. | amplicon |
|---|---|---|---|
| GAPDH | F: CGATCCCGCT AACATCAAAT R: GGATGCAGGG ATGATGTTCT | XR_009174.1 | 460 |

TABLE 1-continued

Primer sequences for RT-PCR

| Gene | Sequence | Accession No. | amplicon |
|---|---|---|---|
| PPAR-γ | F: GTTCATGCTT GTGAAGGATGC R: ACTCTGGGTT CAGCTGGTCG | NM_011146.2 | 249 |
| Adiponectin | F: CGCCTTATGT GTATCGCTCAG R: TGCATAGAGT CCATTGTGGTCCC | NM_009605.4 | 390 |

Semi-quantitative RT PCR 7.14 Reverse Transcriptase Polymerase Chain Reaction (RT-PCR)

RT-PCR was performed for assessing mRNA levels of Col1 (collagen type I), Cbfa-1 (Core binding factor-1), ALP (Alkaline phosphatase), OPN (osteopontin), BMP 2 (Bone morphogenic protein 2), OPG (Osteoprotegrin), and OCN (Osteocalcin). The house-keeping gene GAPDH (Glyceraldehyde-3-phosphate dehydrogenase) was used as the internal control in this study. RNAs were extracted at 0-, 4-, 8-, 12-, 24-, and 48 h. Total RNA was extracted using TRIzol reagent (Invitrogen). A single step RT PCR kit (Qaigen) was used to perform RT-PCR according to the manufacturer's instructions. Following gene specific primer pairs were used (Table 2).

TABLE 2

Primer sequences for RT-PCR

| Gene | Sequence | Accession No. | amplicon |
|---|---|---|---|
| GAPDH bp | F: CGATCCCGCT AACATCAAAT R: GGATGCAGGG ATGATGTTCT | XR_009174.1 | 460 |
| OPG bp | F:TGGCACACAGT GATGAATGCG R:GCTGGAAAGTT TGCTCTTGCG | U94330.1 | 550 |
| Cbfa-1 bp | F:GCCGGGAATGA TGAGAACTA R:GGACCGTCCAC TGTCACTTT | XM_001066909.1 | 199 |
| Col 1 bp | F:TAAAGGGTCAT CGTGGCTTC R:ACTCTCCGCTC TTCCAGTCA | BC133728.1 | 499 |
| OPN bp | F:AAGCCTGACCC ATCTCAGAA R:GCAACTGGGAT GACCTTGAT | M99252.1 | 481 |
| OCN bp | F:AGCGACTCTGA GTCTGACAAA R:AACGGTGGTGC CATAGATGCG | M25490.1 | 524 |
| BMP 2 bp | F:ACTGCGGTCTC CTAAAGGTC R:GCGGTACAGGT CGAGCATAT | NM_017178.1 | 250 |
| ALP bp | F:CGTCTCCATGG TGGATTATGC R:TGGCAAAGACC GCCACAT | J03572 | 101 |

7.15 In Vitro Estrogenicity

The expression of alkaline phosphatase is induced in Ishikawa cells in response to estrogen or estrogen like substances (Littlefield et al, *Endocrinology*. 1990 December; 127(6): 2757-62.). Ishikawa cells were plated in 96-well flat bottomed microtiter plates at a density of 5000 cells/well and cultured in phenol red free DMEM containing 10% charcoal treated FCS. After 24 h of plating, cells were serum-starved for 12 h. Thereafter, for testing estrogenicity of compounds, the cells were treated with different concentrations ($10^{-6}$ to $10^{-11}$ M) of pure compounds K058 and K012. Same concentrations of Raloxifene were also used for comparison. Estrogen concentration of $10^{-8}$ M was used as a positive control. Compound treatments were performed for 72 h at 37° C. in $CO_2$ incubator. Experiments were repeated 4 times. For the anti-estrogenicity studies, the compounds K012 and K058 at $10^{-6}$ to $10^{-11}$ M were added with $10^{-8}$ M estrogen. After 72 h of incubation, the media was removed and the plates were washed twice with PBS and dried by tapping, gently. Freeze fracture of cells was achieved by placing the plates at $-70°$ C. for 15, min followed by bringing to room temperature. The plates were then placed on ice and 50 μl of ice cold diethanolamine solution (5 mM P-nitrophenyl phosphate (PNP) and 0.25 mM $MgCl_2$ in 1 M diethanolamine) was added to each well. The plates were then placed at 37° C. for 30 minutes for color (yellow) development is a function of ALP activity. Absorbance was measured at 405 nm.

7.16 Treatment of K058 in Ovariectomized Sprague Dawley Rats

K058 at 1 to 10 mg/kg body weight were given daily by oral route to Sprague Dawley (180-200 g) rats after bilateral ovariectomy (Ovx). This is the most widely used animal model for osteopenia (bone loss) mimicking human condition of post-menopausal bone loss. The extract was given in gum acacia (vehicle). Sham operated rats and Ovx rats were used as controls and given only gum acacia. Each group consisted of 10 rats and the groups were as follows: sham intact, Ovx, Ovx+1 mg/kg K058 and Ovx+5 mg/kg K058. Treatment started 24 h after the surgery and continued for 90 days. After 90 days, the rats were first acclimatized and then kept in metabolic cages with no food but only water for 24 h to collect urine samples. After 24 h, rats were returned to the cages with food and water ad libitum with oral administration of the extract as before foe an additional 24 hour. Rats were then euthanized and autopsied to collect blood, bones (tibia, femur, L1-L4 vertebrae) and uterus.

7.17 Bone Mineral Density (BMD)

Bone mineral density of femur (global, head, neck), tibia (global, head, tibio-fibular separation point) and lumber vertebra (LV1, LV2, LV3, LV4) was determined by DEXA.

7.18 Treatment of K058 in Immature Sprague Dawley Rats

Female Sprague Dawley rats at weaning (~21 d old) were divided into two groups consisting of 10 rats per group. Control rats were treated with gum acacia (vehicle) and the other group was treated with K058 at 5 mg/kg body weight. All the control and treated rats were given K058 or vehicle daily by oral route in gum acacia for 30 days. After completion of 30 days the rats were euthanized and their bones (femur, tibia, L1-L4 vertebra) were collected.

a) Bone Mineral Density (BMD)

Bone mineral density of femur (global, head, neck), tibia (global, head, tibio-fibular separation point) and lumber vertebra (LV1, LV2, LV3, LV4) was determined by DEXA.

b) Ex-Vivo Culture of Bone Marrow for ALP Quantitation and In Vitro Mineralization from K058 Treated Immature Rats Right femur of control and K058 treated rats were collected aseptically in PBS during autopsy from the rats. Soft tissue was removed, and the ends of the femur was clipped off using sterile scissors, a hole was created in the knee joint end of each bone with a needle, and the marrow was flushed out from the shaft with control medium (CM) which consisted of α-MEM supplemented with 10% fetal calf serum, 100 U/ml penicillin, 100 U/ml streptomycin (Sigma, Chemical Co., St. Louis, Mo., USA). The cells were suspended in this medium, and the suspensions were spun down at 800 rpm for 5 min. Cells were resuspended in fresh CM and counted using a haemocytometer. 100000 and 200000 cells/well were cultured in 48-well and 12-well plates respectively and in a humidified atmosphere, with 5% $CO_2$, at 37° C. in CM supplemented with 10 mM-β-glycerophosphate, 50 μg/ml L-ascorbic acid and $10^{-8}$M dexamethasone. This medium was replaced every other day (John et al., 2002; Connolly. 1995; Gebhart and Lane. 1991; Gurpinar et al., 2003; Lan and Wang, 2003). The cells were maintained for 9 days for ALP activity. ALP activity was determined as described by Akiyama et al. with modifications. Briefly, cells were washed once with PBS, then, ALP activity was measured by adding ALP buffer (1 M diethanolamine, 0.5 mM $MgCl_2$, 1 mg/ml PNPP, pH 9.0), incubating in 37° C., and absorbance (405 nm) was read using a microplate spectrophotometer. Statistical significance was determined by paired two-tailed Student's t-tests.

7.19 Treatment of K012 in Ovariectomized Sprague Dawley Rats

K012 at doses of 1- and 5 mg/kg body weight were given daily by oral route to Sprague Dawley (180-200 g) rats after bilateral ovariectomy (Ovx). The extract was given in gum acacia (vehicle). Sham operated rats and Ovx rats were used as controls and given only gum acacia. Each group consisted of 10 rats and the groups were as follows: sham intact, Ovx, Ovx+1 mg/kg K012 and Ovx+5 mg/kg K012. Treatment started 24 h after the surgery and continued for 90 days. After 90 days, the rats were first acclimatized and then kept in metabolic cages with no food but only water for 24 h to collect urine samples. After 24 h, rats were returned to the cages with food and water ad libitum with oral administration of the extract as before for an additional 24 hour. Rats were then euthanized and autopsied to collect blood, bones (tibia, femur, L1-L4 vertebrae) and uterus.

7.20 Bone Mineral Density (BMD)

Bone mineral density of femur (global, head, neck), tibia (global, head, tibio-fibular separation point) and lumber vertebra (LV1, LV2, LV3, LV4) was determined by DEXA.

8. Prevention of Ovx-Induced Bone Loss by C002

BMD of excised bones measured by DEXA at 90 days of treatment of Ovx rats with the Ethanolic extracts (C002) of *Ulmus wallichiana* (750 mg/kg b.w.). Data revealed that Ovx rats treated with ethanolic extracts at 750 mg/kg has significantly higher BMD in the femur (global, neck and shaft region) compared with Ovx groups treated with vehicle (FIG. 2 A, B, C). In addition, Ovx rats treated with ethanolic extracts at 750 mg/kg have significant higher BMD in LV4 vertebra (the weight bearing vertebra) compared with Ovx groups treated with vehicle (FIG. 2 D). From these results, it is concluded that C002 has bone sparing action under estrogen deficiency.

FIG. 2: Ethanolic extract of *Ulmus wallichiana* reduces Ovx-induced bone loss in rats. BMD was measured by DEXA in excised bones. Ovx rats treated with 750 mg/kg body weight C002 for 90 days were compared with Ovx and sham operated rats treated with vehicle (control). (A) Femur global, (B) femur neck, (C) femur shaft and (D) fourth lumber vertebra (*—P<0.001, —P<0.01, *—P<0.05 when compared with the BMD of sham. a—P<0.001, b—P<0.01, c—P<0.05 when compared with the BMD of ovx control.).

9. Evaluation of Estrogen Agonistic Effect of C002

Ovariectomy results in reduction of uterine weight and agents with estrogen-like action increase uterine weight. Ovx rats treated with Ethanolic extracts (C002) of *Ulmus wallichiana* (750 mg/kg body weight) for 90 days had robust reduction of uterine weight compared with sham operated rats treated with vehicle that was comparable with the Ovx rats treated with vehicle (FIG. 3). Therefore, it is concluded that C002 has no estrogen agonistic action at the uterine level.

FIG. 3: Ethanolic extract of *Ulmus wallichiana* is not estrogenic in rats at uterine level. Uterine wt. of 750 mg/kg b.w. C002 treated rats for 90 days as compared to control sham and ovx rats. *—P<0.001, —P<0.01, *—P<0.05 when compared with uterine wt of sham control rats; c—P<0.001; b—P<0.01; a—P<0.05 when compared with uterine wt of ovx rats.

10. Attainment of PBM in Sprague Dawley Rats a) 21 days old female rats (at weaning) were taken to study the effects of C002 in the attainment of PBM. After 30 days of treatment of C002 at 750 mg/kg body weight, BMD values were found to be significantly more in femur shaft of C002 treated rats compared with control (vehicle) (FIG. 4A). C002 at 750 mg/kg body weight also increased BMD of fourth lumber vertebra in immature rats (FIG. 4 B). We conclude that C002 enhances attainment of PBM in developing female rats.

b) 21 days old female rats (at weaning) were taken to study the effects of the fraction of C002 (F004) in the attainment of PBM. After 30 days of treatment of F004 at 50 mg/kg body weight, BMD values were found to be significantly more in; femur shaft of F004 treated rats compared with control (vehicle) (FIG. 4 A). We conclude that F004, the fraction of C002, promotes attainment of PBM in growing female rats.

FIG. 4: Ethanolic extract and a fraction of *Ulmus wallichiana* promote PBM in immature rats. BMD was measured by DEXA in excised bones. Growing female rats treated with 750 mg/kg C002 and 50 mg/kg 914/F004 (a fraction) were compared with vehicle (control) treated rats. (A) Femur shaft and (B) fourth lumber vertebra (*—P<0.001, —P<0.01, *—P<0.05).

11. Stimulation of Osteoprogenitor Cells by C002

Increase in osteoprogenitor cells in the bone marrow was assessed by ALP activity and mineralization of BMCs following C002 treatment in growing rats, as described above. ALP activity, a measure of osteoblast differentiation was found to be significantly more in the BMCs obtained from C002 treated rats compared with controls (FIG. 5 A). Also, mineralization of BMCs from C002 treated rats was significantly more than controls (vehicle) (FIGS. 5 B & C). We conclude that C002 enhances attainment of PBM by increasing osteoprogenitor cells in the bone marrow.

FIG. 5: Ethanolic extract of *Ulmus wallichiana* promotes osteoprogenitor cells in immature rats. BMCs from growing female rats treated with 750 mg/kg C002 and 50 mg/kg 914/F004 were compared with vehicle (control) treated rats. (A) Alkaline phosphatase assay (for osteoblast differentiation), (B) photomicrographs of alizarin red-S stained cells (for osteoblast mineralization) and (C) quantification of alizarin red-S stain after extraction (*—P<0.001, —P<0.01, *—P<0.05).

12. Stimulation of Osteoblast Differentiation by Four Pure Compounds Isolated from F004

Four pure compounds, K012, K058, K068 and K100, isolated from F004 were tested for their ability to stimulate osteoblast differentiation. Calvarial osteoblasts treated with various concentrations (0.1 nm to 1.0 µM) of these four compounds exhibited 70 to 100% increase in ALP activity compared with control (vehicle) (FIG. 6). We conclude that all 4 isolated pure compounds stimulate osteoblast differentiation that enables osteoblasts to carry out its bone forming function and an important bone anabolic function.

FIG. 6: Four pure compounds from *Ulmus wallichiana* promote differentiation of calvarial osteoblasts in vitro. Calvarial osteoblasts were treated with K012, K058, K068 and K100 at 1 and 100 nm concentrations and ALP production was quantitated. *—P<0.001, —P<0.01, *—P<0.05; N=3.

13. Stimulation of Mineralization of Calvarial Osteoblasts by Four Pure Compounds Isolated from F004

Figure 7C:
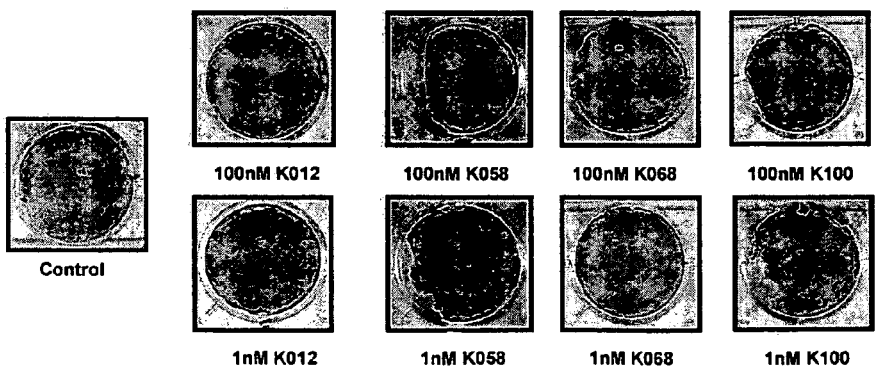

In vitro mineralization of extracellular matrix by rat calvarial (membranous bone) osteoblast cells was assayed by Alizarin staining & extraction and Von kossa staining. A significant increase in mineralization was with all 4 compounds (1 nm and 100 µM concentrations) (FIG. 7). Alizarin red staining, a measure of nascent calcium deposition, was found to be increased by 10 to 25% in osteoblasts treated with K012, K058, K068, and K100, compared with control (vehicle) (FIGS. 7A & B). Von kossa which reacts with phosphate in acidic condition and not with calcium and is a measure of mineralized nodules, was also found to be increased in osteoblasts treated with K012, K058, K068 and K100, compared with controls (vehicle) (FIG. 7C). We conclude that all 4 compounds promote amount of calcification and mineralized bone nodule formation in osteoblasts derived from membranous (calvarial) bone, which are important bone anabolic actions.

FIG. 7: Four pure compounds from *Ulmus wallichiana* promote in vitro mineralization of calvarial osteoblasts. Calvarial osteoblasts were treated with K012, K058, K068 and K100 at 1 and 100 nm concentrations. (A) Photomicrograph of osteoblasts stained with alizarin red-S. (B) Quantification of alizarin red-S stain after its extraction (*—P<0.001, —P<0.01, *—P<0.05). (C) Photomicrograph of osteoblasts stained by von kossa method.

14. Stimulation of Proliferation of Calvarial Osteoblasts by K058

K058 from 10 nm to 1.0 µM stimulated BrdU incorporation (a measure of cellular proliferation) of semi-confluent cultures of calvarial osteoblasts by 25 to 75% (FIG. 8). We conclude that K058 exerts mitogenic effect on osteoblasts, which is an important bone anabolic action.

FIG. 8: K058 promotes proliferation of calvarial osteoblasts. Calvarial osteoblasts were treated with K058 at 1 and 100 nM concentration and BrdU cell proliferation assay was performed. *—<0.001, —P<0.01, *—P<0.05; N=3.

15. Stimulation of Mineralization of BMCs by Four Pure Compounds Isolated From F004

Studies have shown that phytoestrogen, genistein can enhance the commitment and differentiation of BMCs towards the osteoblast lineage (Heim et al, *Endocrinology.* 2004 February; 145(2):848-59.). Bone growth (modeling) and maintenance (remodeling) take place, in cortical and trabecular bones, which contain marrow. We observed that K012, K058, K068, and K100 stimulated mineralization of bone marrow osteoblasts from 1 nM and 100 nM concentrations as assessed by alizarin red staining method (FIGS. 9 A & B). We conclude that all 4 compounds enhance mineralization of BMCs, which is required for their osteogenic action in the skeletal growth and maintenance.

FIG. 9: Four pure compounds from *Ulmus wallichiana* promote in vitro mineralization of BMCs. BMCs treated with K012, K058, K068 and K100 at 1 and 100 nm concentrations and mineralization was performed. (A) Photomicrograph of cells stained with alizarin red-S. (B) Quantification of alizarin red-S stain after its extraction (*—P<0.001, —P<0.01, *—P<0.05).

16 A. In Vitro Inhibition of Adipogenesis in 3T3 L1 Cells by K068 and K100

A well-recognized aspect of postmenopausal and aging-induced bone loss is increase in bone marrow adipogenesis as increased formation of adipocytes from the common pool of mesenchymal stem cells in the bone marrow will result in formation of fewer osteoblasts. Therefore, inhibition of adipocyte differentiation is a major therapeutic approach for osteoporosis. 3T3-L1 is a murine preadipocyte that was used to study the effects of K068 and K100 in adipocyte differentiation. Data show that K068 and K100 at 1 µM, 100 nM and 1 nm concentrations significantly inhibited adipocyte differentiation (FIG. 10 A). We conclude that K068 and K100 have anti-adipogenic effect.

16 B. Downregulation of mRNA Levels of Adipogenic Genes in 3T3-L1 by K068 & K100

3T3-L1 cells were treated with K068 and K100 at $10^{-7}$ & $10^{-9}$M concentrations for 8 d (time of adipocyte formation). Semi-quantitative RT-PCR revealed decreased mRNA levels of PPAR-γ and adiponectin (FIG. 10 B). We conclude that K068 & K100 exert antiadipogenic action by down regulating expression of various genes that promote adipocyte differentiation.

FIG. 10: K068 and K100 inhibit adipogenic differentiation of 3T3-L1 murine preadipocytes. (A) 3T3-L1 cells were treated with K068 and K100 at 1 µM, 100 nM and 1 nM concentrations and oil red-O staining was performed. Stain was extracted and quatitated. *—P<0.001, —P<0.01, *—P<0.05; N=3. (B) Semi-quantitative RT PCR of various adipocyte differentiation-specific genes following the treatment of 3T3-L1 preadipocyte cell with 100 nM and 1 nM of both K068 and K100 for 8 d (time of adipocyte differentiation). GAPDH was used as RNA loading control. Representative gel picture of three independent experiments with similar results.

TABLE 3

Summary of the in vitro effects of the pure compounds isolated from *Ulmus wallichiana*

K058 - Promoted osteoblast proliferation, differentiation and mineralization.
K012 - Promoted osteoblast differentiation and mineralization.
K068 - Promoted osteoblast differentiation, mineralization and have anti-adipogenic activity in 3T3 L1 cell line.
K100 - Promoted osteoblast differentiation, mineralization and have anti-adipogenic activity in 3T3 L1 cell line.

17. Upregulation of mRNA Levels of Osteogenic Genes in Osteoblasts by K058

Calvarial osteoblasts were treated with K058 at $10^{-7}$ M concentration from 0 to 48 h. Semi-quantitative RT-PCR revealed increased mRNA levels of collagen I (COL-1), core binding factor-1 (Cbfa-1), Alkaline phosphatase (ALP) and osteocalcin (OCN), and bone morphogenic protein-2 (BMP-2) (FIG. 11). Osteoprotegrin (OPG), the most potent anti-osteoclastogenic cytokine, secreted from osteoblasts. K058 at $10^{-7}$ M increased mRNA levels of OPG in calvarial osteoblasts (FIG. 11). We conclude that K058 exerts osteogenic action by upregulating synthesis of various genes that promote osteoblast functions and inhibiting osteoclast function.

FIG. 11: K058 increases mRNA levels of various osteoblast-specific genes. Semi-quantitative RT PCR of various osteoblast mRNAs following the treatment of calvarial osteoblasts with 100 nM of K058 at various time points. GAPDH was used as internal loading control. Representative gel picture of three independent experiments with similar results.

18. In Vitro Estrogenic Nor Anti-Estrogenic Profiles of K012 and K058

Ishikawa cells are human endometrial cancer cells that express high levels of estrogen receptors and responds to estrogen by increasing ALP levels. Ishikawa cells treated with increasing concentrations of K012 and K058 ($10^{-11}$ to $10^{-6}$ M) exhibited no increase in ALP levels whereas $10^{-8}$M 17β-estradiol stimulated ALP activity by ~25.0 fold over controls (vehicle treated cells) (FIG. 12 A). In addition, K012 and K058 at concentrations ranging from $10^{-11}$ to $10^{-6}$ M did not inhibit increase in ALP activity stimulated by 17β-estradiol (FIG. 12 B). We conclude that K012 and K058 do not possess estrogen agonistic or anti-estrogenic actions.

FIG. 12: K058 and K012 do not possess estrogenicity and anti-estrogenicity in vitro. Ishikawa cells treated with 17β-estradiol stimulates ALP production. (A) Robust increases in ALP with $10^{-8}$ M 17β-estradiol compared with control. K058, K012 and raloxifene at various concentrations have no response. (B) ALP levels with various concentrations of K012, K058 and raloxifene in the presence of $10^{-8}$ M 17β-estradiol.

19. K058 Reduces Ovx-Induced Bone Loss

BMD of excised bones measured by DEXA at 90 days of treatment of Ovx rats with K058 (1.0-5.0 mg/kg body weight). Data revealed that Ovx rats treated with 1.0-5.0 mg/kg has significantly higher BMD in femur (global, neck and shaft) compared with Ovx group treated with vehicle (FIGS. 13 A, B & C). K058 at 1.0&5.0 mg/kg body weight dose also exhibited higher BMD in the weight bearing, L4 vertebra (FIG. 13 D) and increased BMD in tibia head at 5 mg/kg body weight compared with Ovx group treated with vehicle (FIG. 13 E). From these results, it is concluded that K058 has bone sparing action under estrogen deficiency.

FIG. 13: K058 reduces OVx-induced bone loss in rats. BMD was measured by DEXA in excised bones. Ovx rats treated with 1.0&5.0 mg/kg K058 for 90 days were compared with Ovx and sham operated rats treated with vehicle (control). (A) Femur global, (B) femur neck, (C) femur shaft, (D) fourth lumber vertebra and (E) tibia head (*—$P<0.001$, —$P<0.01$, *—$P<0.05$ when compared with the BMD of sham. a—$P<0.001$, b—$P<0.01$, c—$P<0.05$ when compared with the BMD of Ovx control).

20. In Vivo Estrogen Agonistic Profile of K058

Ovariectomy results in reduction of uterine weight and agents with estrogen-like action increase uterine weight. Ovx rats treated with K058 (1.0&5.0 mg/kg body weight) for 90 days had robust reduction of uterine weight compared with sham operated rats treated with vehicle that was comparable with the Ovx rats treated with vehicle (FIG. 14). Therefore, it is concluded that K058 has no estrogen agonistic action at the uterine level.

FIG. 14: K058 is not estrogenic in rats at uterine level. Uterine wt of 1.0&5.0 mg/kg body weight K058 treated rats for 90 days was compared with uterine wt. of control sham and ovx rats. *—$P<0.001$, —$P<0.01$, *—$P<0.05$ when compared with uterine wt of sham control rats, c—$P<0.001$, b—$P<0.01$, a—$P<0.05$ when compared with uterine wt of ovx rats.

21. Attainment of Peak Bone Mass in Immature Rats by K058

21 days old female rats (at weaning) were taken to study the effects of K058 in the attainment of PBM. After 30 days of treatment of K058 at 5 mg/kg body weight, BMD values were found to be significantly more in shaft region of femur compared with control (vehicle) (FIG. 15). We conclude that K058 enhance attainment of PBM in developing female rats.

FIG. 15: K058 promotes PBM in immature rats. BMD was measured by DEXA in excised bones. Growing female rats treated with 5 mg/kg K058 was compared with vehicle (control) treated rats. BMD in femur shaft is shown (*—$P<0.001$, —$P<0.01$, *—$P<0.05$).

22. Stimulation of Osteoprogenitor Cells by K058

Increase in osteoprogenitor cells in the bone marrow was assessed by ALP activity and mineralization of BMCs following K058 treatment (5.0 mg/kg body weight) in growing rats, as described above. ALP activity, a measure of osteoblast differentiation was found to be significantly more in the BMCs obtained from K058 treated rats (5.0 mg/kg body weight) compared with controls. (FIG. 16 A). Also, mineralization of BMCs from K058 treated rats was significantly more than controls (vehicle) (FIGS. 16 B & C). We conclude that K058 enhances attainment of PBM by increasing osteoprogenitor cells in the bone marrow.

FIG. 16: K058 promotes osteoprogenitor cells in immature rats. BMCs from growing female rats treated with 5 mg/kg K058 for 30 days was compared with vehicle (control) treated rats. (A) Alkaline phosphatase assay, (B) photomicrographs of alizarin red-S stained cells and (C) quantification of alizarin red-S stain after extraction (*—$P<0.001$, —$P<0.01$, *—$P<0.05$).

23. K012 Reduces Ovx-Induced Bone Loss

BMD of excised bones measured by DEXA at 90 days of treatment of Ovx rats with K012 (1.0-5.0 mg/kg b.w.). Data revealed that Ovx rats treated with 5.0 mg/kg has significantly higher BMD in femur neck, tibia global, tibia head and tibio-fibular separation point (TFSP) compared with Ovx group treated with vehicle (FIGS. 17 A, B, C & D). K012 at 5.0 mg/kg body weight dose also exhibited higher BMD in the global and second lumber vertebra (FIGS. 17 E & F) compared with Ovx group treated with vehicle. An increase in BMD was also seen in TFSP in rats treated with K012 at 1.0 mg/kg body weight (FIG. 17 D) when compared with Ovx group treated with vehicle. From these results, it is concluded that K012 has bone sparing action under estrogen deficiency.

FIG. 17: K012 reduces OVx-induced bone loss in rats. BMD was measured by DEXA in excised bones. Ovx rats treated with 1.0&5.0 mg/kg K012 for 90 days were compared with Ovx and sham operated rats treated with vehicle (control). (A) Femur neck, (B) tibia global, (C) tibia head, (D) tibio-fibular separation point (E) lumber vertebra global, and (F) Second lumber vertebra (*—$P<0.001$, —$P<0.01$, *—$P<0.05$ when compared with the BMD of sham. a—$P<0.001$, b—$P<0.01$, c—$P<0.05$ when compared with the BMD of ovx control).

24. In Vivo Estrogen Agonistic Profile of K012

Ovariectomy results in reduction of uterine weight and agents with estrogen-like action increase uterine weight. Ovx rats treated with K012 (1.0&5.0 mg/kg body weight) for 90 days had robust reduction of uterine weight compared with sham operated rats treated with vehicle that was comparable with the Ovx rats treated with vehicle (FIG. 18). Therefore, it is concluded that K012 has no estrogen agonistic action at the uterine level.

FIG. 18: K012 is not estrogenic in rats at uterine level. Uterine wt of 1.0&5.0 mg/kg body weight K012 treated rats for 90 days was compared with uterine wt. of control sham and ovx rats. (*—$P<0.001$, —$P<0.01$, *—$P<0.05$ when compared with uterine wt of sham control rats, c—$P<0.001$, b—$P<0.01$, a—$P<0.05$ when compared with uterine wt of ovx rats).

We claim:
1. A bioactive extract/fraction from *Ulmus wallichiana* useful for the treatment of post-menopausal osteoporosis wherein said extract/fraction comprises marker compounds of general formula 2,

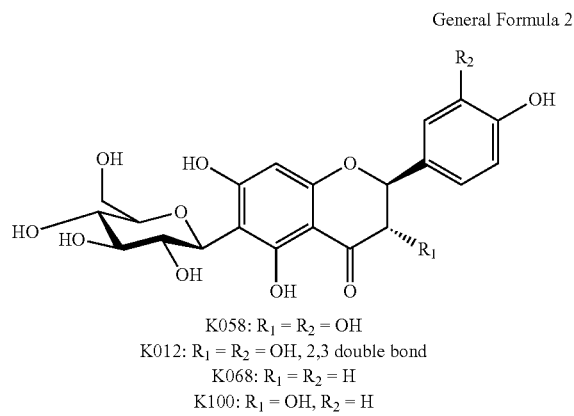

General Formula 2

K058: $R_1 = R_2 = OH$
K012: $R_1 = R_2 = OH$, 2,3 double bond
K068: $R_1 = R_2 = H$
K100: $R_1 = OH, R_2 = H$ wherein the marker compounds K012, K058, K068, K100 ranges 6.7-12%, 1.7-4.5%, 0.6-1.2%, 1.7-4.5% by weight respectively in alcoholic extract.

2. A bioactive extract as claimed in claim 1 wherein, the extract obtained from alcoholic extraction of *Ulmus wallichiana* comprises 6.7-9% by weight of K012, 3.3-4.5% by weight of K058, 0.6-0.7% by weight of K068, and 1.7-2.6% by weight of K100.

3. A bioactive fraction as claimed in claim 1 wherein acetone soluble fraction obtained from alcoholic extract comprises 7.9-12% by weight of K012, 1.7-3.0% by weight of K058, 0.7-1.2% by weight of K068, and 2.5-4.5% by weight of K100.

4. A bioactive fraction as claimed in claim 1 wherein the alcoholic fraction has bone sparing action under estrogen deficiency.

5. A bioactive fraction as claimed in claim 1 wherein the alcoholic fraction enhances attainment of peak bone mass by increasing osteoprogenitor cells in the bone marrow.

6. A bioactive fraction as claimed in claim 1 wherein the bioactive extract/fraction is obtained from plant parts selected from the group consisting of stem, bark and twigs of *Ulmus wallichiana*.

7. A method for the treatment of post-menopausal osteoporosis comprising administering to a subject in need thereof a therapeutically effective amount of a bioactive extract/fraction of claim 1 obtained from *Ulmus wallichiana*.

8. The method as claimed in claim 7 wherein the effective dose of alcoholic extract ranges between 500-750 mg/kg.

9. The method as claimed in claim 7 wherein the compounds of formula 2, K012, K058, K068, K100 exhibit 70 to 100% increase in alkaline phosphatase activity compared with control in calvarial osteoblasts treated at a concentration ranging between 0.1 nM to 1.0 mM.

10. The method as claimed in claim 7 wherein the compounds of formula 2 increase nascent calcium deposition by 10 to 25% in osteoblasts treated with K012, K058, K068, and K100, compared with control.

11. The method as claimed in claim 7 wherein the compounds of formula 2 enhance mineralization of bone marrow cells which is required for their osteogenic action in skeletal growth and maintenance.

12. The method as claimed in claim 7 wherein the compounds of formula 2 are used in combination in the ratios ranging between 0.25-1.0 by weight of K068: 1.0-5.0 by weight of K100: 2.5-7.5 by weight of K058: 5.0-12.5 by weight of K012.

13. The method as claimed in claim 7 wherein the compounds of formula 2, K012, K058, promote osteoblast proliferation, differentiation and mineralization.

14. The method as claimed in claim 7 wherein the compounds of formula 2, K068, and K100, promote osteoblast differentiation, mineralization and have anti-adipogenic activity in 3T3 L1 cell line.

15. The method as claimed in claim 7 wherein K058 exerts osteogenic action by upregulating synthesis of various genes selected from the group COL-1, Cbfa-1, ALP, OCN, BMP-2 that promote osteoblast functions and inhibiting osteoclast function.

16. The method as claimed in claim 7 wherein K058 stimulated BrdU incorporation of semi-confluent cultures of calvarial osteoblasts by 25 to 75% at a concentration ranging between from 10 nM to 1.0 mM.

17. A pharmaceutical composition comprising an effective amount of bioactive extract/fraction from *Ulmus wallichiana* as claimed in claim 1, optionally along with one or more pharmaceutically acceptable additives, carriers and diluents.

18. A pharmaceutical composition as claimed in claim 17, wherein the diluents used is selected from the group consisting of starch, lactose, and dicalcium phosphate.

19. A pharmaceutical composition as claimed in claim 17, wherein the pharmaceutically acceptable additive is selected from the group consisting of talc, magnesium stearate, calcium stearate, solid polyethylene glycols, sodium lauryl sulphate and combinations thereof.

20. A pharmaceutical composition as claimed in claim 17, wherein a dosage of said composition is administered at a unit dose of at least 500- to 750 mg/Kg body weight for alcoholic extract.

21. A pharmaceutical composition as claimed in claim 17, wherein an alcoholic extract is derived from the *Ulmus wallichiana* having bone sparing action under estrogen deficiency, having no estrogen antagonistic action at the uterine level, enhancing attainment of peak bone mass by increasing osteoprogenitor cells in the bone marrow in developing female rats.

22. A method of treating post-menopausal osteoporosis in a subject, wherein the said method comprises the step of administering to the subject in need thereof a pharmaceutical composition as claimed in claim 17.

23. The method as claimed in claim 22 wherein the pharmaceutical composition may be administered by oral, intravenous, subcutaneous, intra-peritoneal or intramuscular route.

24. A process for the preparation of an extract/fraction of marker compounds of claim 1 from *Ulmus wallichiana*, wherein the process comprises:

(a) providing the plant *Ulmus wallichiana*,
(b) powdering of the plant material,
(c) extracting the powdered plant material with protic solvent at room temperature,
(d) filtering the extract,
(e) concentrating the extract under reduced pressure,
(f) triturating the extract with hexane to remove the non-polar constituents,
(g) drying the residue under vacuum to obtain free flowing powder to give the desired extract,
(h) dissolving the extract obtained in step (g) in water,
(i) precipitating the aqueous extract by addition of n-butanol,
(j) filtering the white precipitate to obtain compound K058,
(k) crystallizing the compound of step (j) with mixture of methanol and ethyl acetate,
(l) filtering the crystallized compound,
(m) drying the compound to obtain K058 in free flowing white powdered form,
(n) concentrating the filtrate obtained in step (l) and triturating with acetone to obtain acetone soluble fraction, and
(o) isolating the compounds K012, K068, K100 from the acetone soluble fraction of step (n) by conventional chromatographic methods.

25. A process as claimed in claim 24, wherein the alcohol used for extraction is selected from the group consisting of methanol, ethanol, propanol or a suitable combination thereof.

26. A process as claimed in claim 24, wherein the solvents used for trituration is selected from acetone, ethyl methyl ketone, dichloromethane, chloroform, ethyl acetate, methanol or a suitable combination thereof.

27. A method of treating post-menopausal osteoporosis comprising administering a therapeutically effective amount of a compound of the formula

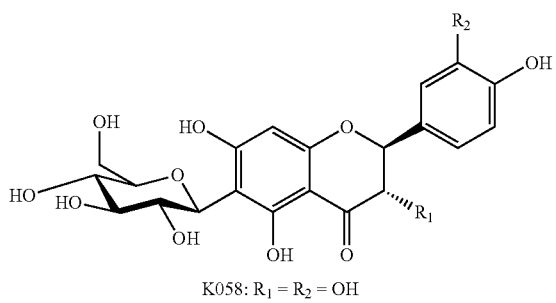

K058: $R_1 = R_2 = OH$ to a subject in need thereof, wherein said compound is obtained from *Ulmus wallichiana*.

28. A method of treating post-menopausal osteoporosis comprising administering a therapeutically effective amount of a compound of the formula

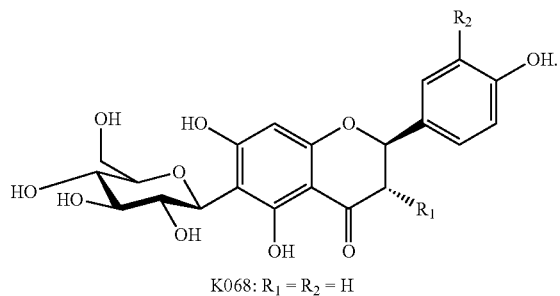

K068: $R_1 = R_2 = H$ to a subject in need thereof, wherein said compound is obtained from *Ulmus wallichiana*.

29. A method of treating post-menopausal osteoporosis comprising administering a therapeutically effective amount of a compound of the formula

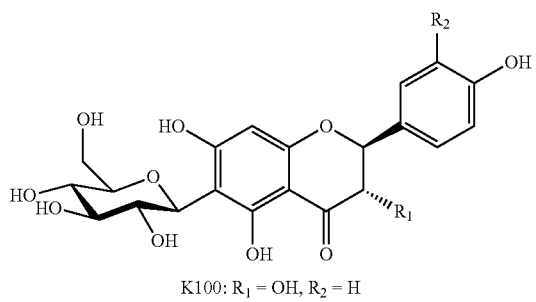

K100: $R_1 = OH, R_2 = H$ to a subject in need thereof, wherein said compound is obtained from *Ulmus wallichiana*.

* * * * *